United States Patent
Risk, Jr. et al.

(10) Patent No.: US 7,678,090 B2
(45) Date of Patent: Mar. 16, 2010

(54) WOUND TREATMENT APPARATUS

(76) Inventors: James R. Risk, Jr., 10861 N. Private Rd. 23 W., Fountaintown, IN (US) 46130; Robert Petrosenko, 30 Belmont Pl. West, Batesville, IN (US) 47006

( * ) Notice: Subject to any disclaimer, the term of this patent is extended or adjusted under 35 U.S.C. 154(b) by 0 days.

(21) Appl. No.: 10/997,612

(22) Filed: Nov. 24, 2004

(65) Prior Publication Data
US 2005/0090787 A1   Apr. 28, 2005

Related U.S. Application Data

(60) Division of application No. 10/159,720, filed on May 31, 2002, now Pat. No. 6,824,533, which is a continuation-in-part of application No. 09/725,666, filed on Nov. 29, 2000, now Pat. No. 6,755,807.

(60) Provisional application No. 60/167,753, filed on Nov. 29, 1999.

(51) Int. Cl.
  *A61F 13/00*   (2006.01)
  *A61M 35/00*   (2006.01)
  *E05B 3/00*    (2006.01)
  *A61M 1/00*    (2006.01)

(52) U.S. Cl. .................. 604/305; 604/304; 604/289; 604/313; 604/35; 292/358

(58) Field of Classification Search ......... 604/317–331, 604/305, 35, 306–308, 540–544, 606, 902; D24/121; D7/332; 292/358
See application file for complete search history.

(56) References Cited

U.S. PATENT DOCUMENTS

| 774,529 | A | 11/1904 | Nieschang |
|---|---|---|---|
| 1,000,001 | A | 8/1911 | Holz |
| 1,355,846 | A | 10/1920 | Rannells |
| 1,385,346 | A | 7/1921 | Taylor |
| 1,709,520 | A * | 4/1929 | Chandler ................ 292/259 R |
| 1,936,129 | A | 11/1933 | Fisk |
| 2,078,180 | A | 4/1937 | Kronenberg |
| 2,195,771 | A | 4/1940 | Estler |
| 2,221,758 | A | 11/1940 | Elmquist |
| 2,338,339 | A | 1/1944 | LaMere et al. |
| 2,443,481 | A | 6/1948 | Sene |

(Continued)

FOREIGN PATENT DOCUMENTS

AU    550575 A1    8/1982

(Continued)

OTHER PUBLICATIONS

Davydov, et al., Vestn. Khir., Sep. 1988—"Vacuum Therapy in the treatment of Acute Suppurative Diseases Of Soft Tissues and Suppurative Wounds" (English translation by R. McElroy Translation Co., Austin, Texas.

(Continued)

*Primary Examiner*—Tatyana Zalukaeva
*Assistant Examiner*—Susan Su

(57) ABSTRACT

A control unit is adapted for use with a vacuum wound bandage. The control unit has a canister to collect waste material from the vacuum wound bandage, a fluid source to irrigate the wound, and a door to at least partially cover the fluid source.

6 Claims, 17 Drawing Sheets

U.S. PATENT DOCUMENTS

| | | | |
|---|---|---|---|
| 2,547,758 A | 4/1951 | Keeling | 128/349 |
| 2,560,915 A | 7/1951 | Bamberger | 128/350 |
| 2,573,791 A | 11/1951 | Howells | |
| 2,577,945 A | 12/1951 | Atherton | |
| 2,632,443 A | 3/1953 | Lesher | |
| 2,682,873 A | 7/1954 | Evans et al. | |
| 2,910,763 A | 11/1959 | Lauterbach | 128/72.2 |
| 2,969,057 A | 1/1961 | Simmons | 128/2 |
| 3,026,874 A | 3/1962 | Stevens | |
| 3,066,672 A | 12/1962 | Crosby, Jr. et al. | 128/276 |
| 3,315,665 A | 4/1967 | MacLeod | |
| 3,367,332 A | 2/1968 | Groves | |
| 3,382,867 A | 5/1968 | Reaves | |
| 3,430,631 A | 3/1969 | Abramson | 128/350 |
| 3,492,991 A | 2/1970 | Dyer, Jr. | |
| 3,520,300 A | 7/1970 | Flower, Jr. | |
| 3,528,416 A | 9/1970 | Chamberlain | |
| 3,568,675 A | 3/1971 | Harvey | |
| 3,585,742 A * | 6/1971 | Tyler | 40/642.02 |
| 3,599,639 A | 8/1971 | Spotz | |
| 3,610,238 A | 10/1971 | Rich, Jr. | |
| 3,623,087 A | 11/1971 | Gallichotte | |
| 3,648,692 A | 3/1972 | Wheeler | |
| 3,682,180 A | 8/1972 | McFarlane | 128/350 |
| 3,683,894 A * | 8/1972 | Villari | 600/580 |
| 3,721,244 A | 3/1973 | Elmaleh | |
| 3,752,158 A | 8/1973 | Kariher | 128/278 |
| 3,753,439 A | 8/1973 | Brugarolas et al. | 128/350 |
| 3,782,377 A | 1/1974 | Rychlik | |
| 3,812,972 A | 5/1974 | Rosenblum | |
| 3,814,095 A | 6/1974 | Lubens | |
| 3,823,720 A | 7/1974 | Tribble | 128/350 |
| 3,826,254 A | 7/1974 | Mellor | 128/133 |
| 3,831,588 A | 8/1974 | Rinder | |
| 3,860,008 A | 1/1975 | Miner et al. | 128/350 |
| 3,874,387 A | 4/1975 | Barbieri | |
| 3,903,882 A | 9/1975 | Augurt | |
| 3,924,624 A | 12/1975 | Schachet | 128/276 |
| 3,935,863 A | 2/1976 | Kliger | |
| 3,954,105 A | 5/1976 | Nordby et al. | |
| 3,982,546 A | 9/1976 | Friend | |
| 4,004,590 A * | 1/1977 | Muriot | 604/326 |
| 4,013,076 A * | 3/1977 | Puderbaugh et al. | 604/320 |
| RE29,319 E | 7/1977 | Nordby et al. | |
| RE29,321 E | 7/1977 | Holbrook | |
| 4,058,123 A | 11/1977 | May | 128/278 |
| 4,080,970 A | 3/1978 | Miller | |
| 4,096,853 A | 6/1978 | Weigand | 128/2 |
| 4,112,947 A | 9/1978 | Nehring | |
| 4,139,004 A | 2/1979 | Gonzalez, Jr. | |
| 4,149,541 A | 4/1979 | Gammons et al. | |
| 4,165,748 A | 8/1979 | Johnson | 128/348 |
| 4,178,974 A | 12/1979 | Levin | |
| 4,184,510 A | 1/1980 | Murry et al. | 137/565 |
| 4,191,204 A | 3/1980 | Nehring | |
| 4,224,941 A | 9/1980 | Stivala | |
| 4,233,969 A | 11/1980 | Lock et al. | 128/156 |
| 4,245,630 A | 1/1981 | Lloyd et al. | 128/155 |
| 4,250,882 A | 2/1981 | Adair | |
| 4,256,109 A | 3/1981 | Nichols | 128/276 |
| 4,261,363 A | 4/1981 | Russo | 128/350 |
| 4,275,721 A | 6/1981 | Olson | |
| 4,284,079 A | 8/1981 | Adair | 128/295 |
| 4,297,995 A | 11/1981 | Golub | |
| 4,333,468 A | 6/1982 | Geist | 128/348 |
| 4,341,209 A | 7/1982 | Schaar | |
| 4,373,519 A | 2/1983 | Errede et al. | |
| 4,373,659 A | 2/1983 | Cornell et al. | |
| 4,382,441 A | 5/1983 | Svedman | |
| 4,392,853 A | 7/1983 | Muto | 604/171 |
| 4,392,858 A | 7/1983 | George et al. | 604/187 |
| 4,399,816 A | 8/1983 | Spangler | |
| 4,419,097 A | 12/1983 | Rowland | 604/174 |
| 4,457,755 A | 7/1984 | Wilson | |
| 4,460,370 A | 7/1984 | Allison et al. | |
| 4,465,062 A | 8/1984 | Versaggi et al. | |
| 4,465,485 A | 8/1984 | Kashmer et al. | 604/320 |
| 4,469,092 A | 9/1984 | Marshall et al. | |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,525,156 A | 6/1985 | Benusa et al. | 604/28 |
| 4,525,166 A | 6/1985 | Leclerc | |
| 4,525,374 A | 6/1985 | Vaillancourt | 427/2 |
| 4,533,352 A | 8/1985 | Van Beek et al. | |
| 4,533,419 A | 8/1985 | Pieslak et al. | |
| 4,540,412 A | 9/1985 | Van Overloop | |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | |
| 4,569,348 A | 2/1986 | Hasslinger | 604/179 |
| 4,569,674 A | 2/1986 | Phillips et al. | |
| 4,573,965 A | 3/1986 | Russo | |
| 4,579,555 A | 4/1986 | Russo | |
| 4,605,399 A | 8/1986 | Weston et al. | |
| 4,608,041 A | 8/1986 | Nielsen | |
| 4,614,794 A | 9/1986 | Easton et al. | 530/356 |
| 4,624,656 A | 11/1986 | Clark et al. | |
| 4,633,863 A | 1/1987 | Filips et al. | |
| 4,637,819 A | 1/1987 | Oullette et al. | |
| 4,640,688 A | 2/1987 | Hauser | 604/352 |
| 4,641,643 A | 2/1987 | Greer | |
| 4,645,492 A | 2/1987 | Weeks | |
| 4,655,210 A | 4/1987 | Edenbaum et al. | |
| 4,655,754 A | 4/1987 | Richmond et al. | |
| 4,661,093 A | 4/1987 | Beck et al. | |
| 4,664,652 A | 5/1987 | Weilbacher | |
| 4,664,662 A | 5/1987 | Webster | |
| 4,667,666 A | 5/1987 | Frysliie | |
| 4,679,590 A | 7/1987 | Hergenroeder | |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,382 A | 1/1988 | Clemens et al. | |
| 4,733,659 A | 3/1988 | Edenbaum et al. | |
| 4,735,606 A | 4/1988 | Davison | |
| 4,735,610 A * | 4/1988 | Akkas et al. | 604/119 |
| 4,740,202 A | 4/1988 | Stacey et al. | |
| 4,743,232 A | 5/1988 | Kruger | |
| 4,747,166 A | 5/1988 | Kuntz | |
| 4,758,220 A | 7/1988 | Sundblom et al. | 604/65 |
| 4,759,354 A | 7/1988 | Quarfoot | |
| 4,765,316 A | 8/1988 | Marshall | |
| 4,778,446 A | 10/1988 | Jensen | |
| 4,778,456 A | 10/1988 | Lokken | |
| 4,787,888 A | 11/1988 | Fox | 604/20 |
| 4,798,578 A * | 1/1989 | Ranford | 604/6.09 |
| 4,820,265 A | 4/1989 | DeSatnick et al. | |
| 4,820,284 A | 4/1989 | Hauri | |
| 4,826,494 A | 5/1989 | Richmond et al. | 604/323 |
| 4,826,949 A | 5/1989 | Stanko | 528/272 |
| 4,834,110 A | 5/1989 | Richard | |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austad | |
| 4,878,901 A | 11/1989 | Sachse | 604/174 |
| 4,890,608 A | 1/1990 | Steer | |
| 4,897,081 A | 1/1990 | Poirier et al. | |
| 4,900,302 A | 2/1990 | Newton | 604/30 |
| 4,902,508 A | 2/1990 | Badylak et al. | 424/95 |

| Patent | Date | Inventor | Ref |
|---|---|---|---|
| 4,906,233 A | 3/1990 | Moriuchi et al. | 604/174 |
| 4,906,240 A | 3/1990 | Reed et al. | |
| 4,915,694 A | 4/1990 | Yamamoto et al. | |
| 4,917,112 A | 4/1990 | Kalt | |
| 4,919,654 A | 4/1990 | Kalt | 604/180 |
| 4,921,492 A | 5/1990 | Schultz et al. | |
| 4,930,997 A | 6/1990 | Bennett | |
| 4,941,882 A | 7/1990 | Ward et al. | |
| 4,953,565 A | 9/1990 | Tachibana et al. | |
| 4,956,178 A | 9/1990 | Badylak et al. | 424/551 |
| 4,957,492 A | 9/1990 | McVay | |
| 4,962,761 A | 10/1990 | Golden | |
| 4,969,880 A | 11/1990 | Zamierowski | |
| 4,969,881 A | 11/1990 | Viesturs | |
| 4,970,298 A | 11/1990 | Silver et al. | 530/356 |
| 4,985,019 A | 1/1991 | Michelson | 604/180 |
| 4,988,336 A | 1/1991 | Kohn | |
| 4,990,144 A | 2/1991 | Blott | |
| 4,991,574 A | 2/1991 | Pocknell | |
| 4,994,022 A * | 2/1991 | Steffler et al. | 604/7 |
| 4,997,425 A | 3/1991 | Shioya et al. | |
| 5,000,172 A | 3/1991 | Ward | |
| 5,000,741 A | 3/1991 | Kalt | |
| 5,002,528 A | 3/1991 | Palestrant | |
| 5,002,529 A | 3/1991 | Cunningham | |
| 5,003,971 A | 4/1991 | Buckley | |
| 5,014,389 A | 5/1991 | Ogilvie et al. | |
| 5,034,003 A | 7/1991 | Denance | |
| 5,034,006 A | 7/1991 | Hosoda et al. | |
| 5,035,865 A * | 7/1991 | Inaba et al. | 422/99 |
| 5,037,397 A | 8/1991 | Kalt et al. | 604/174 |
| 5,042,978 A | 8/1991 | Quenin et al. | |
| 5,045,777 A | 9/1991 | Itagaki | |
| 5,060,662 A | 10/1991 | Farnsworth, III | |
| 5,071,409 A | 12/1991 | Rosenberg | |
| 5,073,172 A | 12/1991 | Fell | |
| 5,080,650 A | 1/1992 | Hirsch et al. | 604/104 |
| 5,086,170 A | 2/1992 | Luheshi et al. | 540/303 |
| 5,086,763 A | 2/1992 | Hathman | |
| 5,086,764 A | 2/1992 | Gilman | |
| 5,100,396 A | 3/1992 | Zamierowski | |
| 5,101,808 A | 4/1992 | Kobayashi et al. | |
| 5,106,362 A | 4/1992 | Gilman | |
| 5,106,629 A | 4/1992 | Cartmell et al. | |
| 5,134,994 A | 8/1992 | Say | 28/200.24 |
| 5,135,518 A | 8/1992 | Vera | |
| 5,146,925 A | 9/1992 | Snow | |
| 5,147,338 A | 9/1992 | Lang et al. | |
| 5,149,331 A | 9/1992 | Ferdman et al. | |
| 5,152,757 A | 10/1992 | Eriksson | |
| 5,160,322 A | 11/1992 | Scheremet et al. | |
| 5,167,613 A | 12/1992 | Karami et al. | |
| 5,167,622 A | 12/1992 | Muto | 604/35 |
| 5,170,781 A | 12/1992 | Loomis | |
| 5,176,502 A | 1/1993 | Sanderson et al. | |
| 5,176,663 A | 1/1993 | Svedman et al. | |
| 5,176,667 A | 1/1993 | DeBring | |
| 5,181,908 A | 1/1993 | Bell | 604/24 |
| 5,189,609 A | 2/1993 | Tivig et al. | |
| 5,197,948 A | 3/1993 | Ghodsian | 604/30 |
| 5,215,522 A | 6/1993 | Page et al. | 604/33 |
| 5,215,539 A | 6/1993 | Schoolman | |
| 5,224,929 A | 7/1993 | Remiszewski | 604/30 |
| 5,228,431 A | 7/1993 | Giarretto | |
| 5,230,350 A | 7/1993 | Fentress | |
| 5,232,453 A | 8/1993 | Plass et al. | 604/180 |
| 5,238,654 A | 8/1993 | Nohl et al. | |
| 5,249,121 A | 9/1993 | Baum et al. | |
| 5,256,418 A | 10/1993 | Kemp et al. | 424/423 |
| 5,261,893 A | 11/1993 | Zamierowski | |
| 5,263,922 A | 11/1993 | Sova et al. | |
| 5,265,605 A | 11/1993 | Afflerbach | |
| 5,275,826 A | 1/1994 | Badylak et al. | 424/551 |
| 5,278,100 A | 1/1994 | Doan et al. | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley et al. | |
| 5,298,015 A | 3/1994 | Komatsuzaki et al. | |
| 5,306,298 A | 4/1994 | Godley, III et al. | |
| 5,314,409 A | 5/1994 | Sarosiek et al. | 604/101 |
| 5,330,452 A | 7/1994 | Zook | |
| 5,335,651 A | 8/1994 | Foster et al. | |
| 5,338,293 A | 8/1994 | Jeppsson et al. | 604/29 |
| 5,342,293 A | 8/1994 | Zanger | |
| 5,342,301 A | 8/1994 | Saab | 604/96 |
| 5,342,376 A | 8/1994 | Ruff | 606/151 |
| 5,344,415 A | 9/1994 | DeBusk et al. | |
| 5,349,965 A | 9/1994 | McCarver | |
| 5,352,463 A | 10/1994 | Badylak et al. | 424/551 |
| 5,358,494 A | 10/1994 | Svedman | |
| 5,370,610 A | 12/1994 | Reynolds | 604/43 |
| 5,372,821 A | 12/1994 | Badylak et al. | 424/551 |
| 5,374,254 A | 12/1994 | Buma | |
| 5,376,252 A | 12/1994 | Ekstrom et al. | |
| 5,380,280 A | 1/1995 | Peterson | |
| 5,395,315 A | 3/1995 | Griep | |
| 5,409,013 A | 4/1995 | Clement | 128/753 |
| 5,413,788 A | 5/1995 | Edwards et al. | |
| 5,419,768 A | 5/1995 | Kayser | |
| 5,431,622 A | 7/1995 | Pyrozyk et al. | |
| 5,437,651 A | 8/1995 | Todd et al. | |
| 5,445,604 A | 8/1995 | Lang | |
| 5,445,833 A | 8/1995 | Badylak et al. | 424/551 |
| 5,447,505 A | 9/1995 | Valentine et al. | |
| 5,449,383 A | 9/1995 | Chatelier et al. | 623/1 |
| 5,451,215 A | 9/1995 | Wolter | |
| 5,451,373 A | 9/1995 | Lewis et al. | |
| 5,478,333 A | 12/1995 | Asherman, Jr. | |
| 5,484,420 A | 1/1996 | Russo | |
| 5,484,427 A | 1/1996 | Gibbons | |
| 5,484,428 A | 1/1996 | Drainville et al. | |
| 5,487,889 A | 1/1996 | Eckert et al. | |
| 5,516,533 A | 5/1996 | Badylak et al. | 424/551 |
| 5,520,652 A | 5/1996 | Peterson | |
| 5,527,293 A | 6/1996 | Zamierowski | |
| 5,531,670 A | 7/1996 | Westby et al. | |
| 5,533,981 A | 7/1996 | Mandro et al. | |
| 5,534,346 A | 7/1996 | Robinson | |
| 5,542,918 A | 8/1996 | Atkinson | |
| 5,549,584 A | 8/1996 | Gross | |
| 5,554,389 A | 9/1996 | Badylak et al. | 424/558 |
| 5,556,375 A | 9/1996 | Ewall | |
| 5,558,639 A | 9/1996 | Gangemi et al. | |
| 5,573,784 A | 11/1996 | Badylak et al. | 424/551 |
| 5,578,022 A | 11/1996 | Scherson et al. | |
| 5,578,662 A | 11/1996 | Bennett et al. | 524/54 |
| 5,607,388 A | 3/1997 | Ewall | |
| 5,621,035 A | 4/1997 | Lyles et al. | 524/404 |
| 5,624,418 A | 4/1997 | Shepard | |
| 5,628,735 A | 5/1997 | Skow | |
| 5,629,186 A | 5/1997 | Yasukawa et al. | 435/177 |
| 5,631,011 A | 5/1997 | Wadstrom | 424/400 |
| 5,635,201 A | 6/1997 | Fabo | |
| 5,636,643 A | 6/1997 | Argenta et al. | |
| 5,641,518 A | 6/1997 | Badylak et al. | 424/551 |
| 5,645,081 A | 7/1997 | Argenta et al. | |
| 5,645,860 A | 7/1997 | Knapp, Jr. et al. | 424/551 |
| 5,655,258 A | 8/1997 | Heintz | |
| 5,656,027 A | 8/1997 | Ellingboe | |
| 5,662,598 A | 9/1997 | Tobin | |
| 5,662,624 A | 9/1997 | Sundstrom et al. | |
| 5,662,625 A | 9/1997 | Westwood | |
| 5,669,892 A | 9/1997 | Keogh et al. | |
| 5,672,151 A | 9/1997 | Calderon-Garciduenãs | 602/21 |
| 5,672,152 A | 9/1997 | Mason et al. | |
| 5,674,193 A | 10/1997 | Hayes | 604/28 |

| | | | |
|---|---|---|---|
| 5,678,564 A | 10/1997 | Lawrence et al. | |
| 5,681,290 A | 10/1997 | Alexander ................. 604/180 | |
| 5,690,815 A | 11/1997 | Krasnoff et al. | |
| 5,695,998 A | 12/1997 | Badylak et al. ............ 435/391 | |
| 5,697,920 A | 12/1997 | Gibbons | |
| 5,711,969 A | 1/1998 | Patel et al. .................. 424/551 | |
| 5,718,955 A | 2/1998 | McGuire et al. | |
| 5,735,833 A | 4/1998 | Olson | |
| 5,741,237 A | 4/1998 | Walker | |
| 5,749,842 A | 5/1998 | Cheong et al. ................ 602/41 | |
| 5,753,267 A | 5/1998 | Badylak et al. ............ 424/551 | |
| 5,755,791 A | 5/1998 | Whitson et al. .............. 623/15 | |
| 5,759,570 A | 6/1998 | Arnold | |
| 5,762,640 A | 6/1998 | Kajiwara et al. | |
| 5,762,966 A | 6/1998 | Knapp, Jr. et al. .......... 424/551 | |
| 5,780,281 A | 7/1998 | Yasukawa et al. .......... 435/176 | |
| 5,782,871 A | 7/1998 | Fujiwara et al. | |
| 5,795,584 A | 8/1998 | Totakura et al. ............. 424/426 | |
| 5,800,383 A | 9/1998 | Chandler et al. ............... 604/35 | |
| 5,817,145 A | 10/1998 | Augustine et al. | |
| 5,827,246 A | 10/1998 | Bowen | |
| 5,827,296 A | 10/1998 | Morris et al. | |
| 5,855,619 A | 1/1999 | Caplan et al. ................ 623/11 | |
| 5,866,414 A | 2/1999 | Badylak et al. ............ 435/325 | |
| 5,881,723 A | 3/1999 | Wallace et al. | |
| 5,902,874 A | 5/1999 | Roby et al. ................. 528/310 | |
| 5,902,875 A | 5/1999 | Roby et al. ................. 528/310 | |
| 5,911,222 A | 6/1999 | Lawrence et al. | |
| 5,914,387 A | 6/1999 | Roby et al. ................. 528/310 | |
| 5,919,476 A | 7/1999 | Fischer et al. | |
| 5,921,972 A | 7/1999 | Skow | |
| 5,928,174 A | 7/1999 | Gibbins | |
| 5,931,304 A | 8/1999 | Hammond ................. 206/570 | |
| 5,941,859 A | 8/1999 | Lerman | |
| 5,942,496 A | 8/1999 | Bonadio et al. ............... 514/44 | |
| 5,947,914 A | 9/1999 | Augustine | |
| 5,951,295 A | 9/1999 | Lyles et al. ............... 433/228.1 | |
| 5,954,680 A | 9/1999 | Augustine | |
| 5,961,480 A | 10/1999 | Augustine | |
| 5,962,427 A | 10/1999 | Goldstein et al. ............. 514/44 | |
| 5,964,721 A | 10/1999 | Augustine | |
| 5,964,723 A | 10/1999 | Augustine | |
| 5,986,163 A | 11/1999 | Augustine | |
| 5,997,568 A | 12/1999 | Liu ............................. 606/228 | |
| 6,010,527 A | 1/2000 | Augustine et al. | |
| 6,013,048 A | 1/2000 | Podany et al. ................. 604/22 | |
| 6,017,493 A | 1/2000 | Cambron et al. | |
| 6,039,724 A | 3/2000 | Seifert et al. | |
| 6,045,518 A | 4/2000 | Augustine | |
| 6,045,541 A | 4/2000 | Matsumoto et al. | |
| 6,051,747 A | 4/2000 | Lindqvist et al. | |
| 6,056,730 A | 5/2000 | Greter | |
| 6,071,254 A | 6/2000 | Augustine | |
| 6,071,267 A | 6/2000 | Zamierowski | |
| 6,071,304 A | 6/2000 | Augustine et al. | |
| 6,080,189 A | 6/2000 | Augustine et al. | |
| 6,080,243 A | 6/2000 | Insley et al. | |
| 6,093,160 A | 7/2000 | Augustine et al. | |
| 6,093,230 A | 7/2000 | Johnson et al. | |
| 6,095,992 A | 8/2000 | Augustine | |
| 6,099,567 A | 8/2000 | Badylak et al. ............... 623/13 | |
| 6,110,197 A | 8/2000 | Augustine et al. | |
| 6,113,561 A | 9/2000 | Augustine | |
| 6,117,111 A | 9/2000 | Fleischmann | |
| 6,135,116 A | 10/2000 | Vogel et al. | |
| 6,142,982 A | 11/2000 | Hunt et al. | |
| 6,143,945 A | 11/2000 | Augustine et al. | |
| 6,149,614 A | 11/2000 | Dunshee et al. | |
| 6,171,344 B1 | 1/2001 | Atala ....................... 623/23.64 | |
| 6,174,306 B1 | 1/2001 | Fleischmann | |
| 6,203,563 B1 | 3/2001 | Fernandez | |
| 6,206,931 B1 | 3/2001 | Cook et al. ............... 623/23.75 | |
| 6,207,875 B1 | 3/2001 | Lindqvist et al. | |
| 6,213,965 B1 | 4/2001 | Augustine et al. | |
| 6,213,966 B1 | 4/2001 | Augustine | |
| 6,217,535 B1 | 4/2001 | Augustine | |
| 6,235,009 B1 | 5/2001 | Skow | |
| 6,235,047 B1 | 5/2001 | Augustine et al. | |
| 6,241,697 B1 | 6/2001 | Augustine | |
| 6,241,698 B1 | 6/2001 | Augustine | |
| 6,241,747 B1 | 6/2001 | Ruff .......................... 606/216 | |
| 6,244,311 B1 | 6/2001 | Hand et al. | |
| 6,248,084 B1 | 6/2001 | Augustine et al. | |
| 6,254,557 B1 | 7/2001 | Augustine et al. | |
| 6,254,580 B1 | 7/2001 | Svedman | |
| 6,259,067 B1 | 7/2001 | Faries, Jr. et al. | |
| 6,264,622 B1 | 7/2001 | Augustine | |
| 6,264,979 B1 | 7/2001 | Svedman | |
| 6,267,740 B1 | 7/2001 | Augustine et al. | |
| 6,283,931 B1 | 9/2001 | Augustine | |
| 6,284,941 B1 | 9/2001 | Cox et al. | |
| 6,287,316 B1 | 9/2001 | Agarwal et al. ............. 606/151 | |
| 6,290,685 B1 | 9/2001 | Insley et al. | |
| 6,293,917 B1 | 9/2001 | Augustine et al. | |
| 6,325,798 B1 | 12/2001 | Edwards et al. ................ 606/41 | |
| 6,345,623 B1 | 2/2002 | Heaton et al. | |
| 6,364,853 B1 | 4/2002 | French et al. ................. 604/35 | |
| 6,394,142 B1 | 5/2002 | Woelfel et al. ............. 138/115 | |
| 6,398,767 B1 | 6/2002 | Fleischmann | |
| 6,410,427 B1 | 6/2002 | Hu ................................ 38/655 | |
| 6,440,427 B1 | 8/2002 | Wadström ................... 424/400 | |
| 6,458,109 B1 | 10/2002 | Henley et al. | |
| 6,471,685 B1 | 10/2002 | Johnson | |
| 6,472,581 B1 | 10/2002 | Muramatsu et al. | |
| 6,488,643 B1 | 12/2002 | Tumey et al. ................. 602/13 | |
| 6,491,682 B2 | 12/2002 | Paderni | |
| 6,491,693 B1 | 12/2002 | Lytinas | |
| 6,493,568 B1 | 12/2002 | Bell et al. .................... 600/323 | |
| 6,500,112 B1 | 12/2002 | Khouri | |
| 6,520,982 B1 | 2/2003 | Boynton et al. | |
| 6,553,998 B2 | 4/2003 | Heaton et al. | |
| 6,557,704 B1 | 5/2003 | Randolph | |
| 6,559,773 B1 | 5/2003 | Berry | |
| 6,599,277 B2 | 7/2003 | Neubert | |
| 6,626,891 B2 | 9/2003 | Ohmstede | |
| 6,638,270 B2 | 10/2003 | Johnson | |
| 6,648,862 B2 | 11/2003 | Watson | |
| 6,663,349 B1 | 12/2003 | Discenzo et al. | |
| 6,685,681 B2 | 2/2004 | Lockwood et al. | |
| 6,691,047 B1 | 2/2004 | Fredericks | |
| 6,695,823 B1 | 2/2004 | Lina et al. | |
| 6,695,824 B2 | 2/2004 | Howard et al. ............... 604/305 | |
| 6,719,779 B2 * | 4/2004 | Daoud ........................ 607/105 | |
| 6,749,592 B2 | 6/2004 | Lord | |
| 6,752,794 B2 | 6/2004 | Lockwood et al. | |
| 6,755,807 B2 | 6/2004 | Risk, Jr. et al. | |
| 6,764,462 B2 | 7/2004 | Risk, Jr. et al. | |
| 6,767,334 B1 | 7/2004 | Randolph .................... 604/35 | |
| 6,800,074 B2 | 10/2004 | Henley et al. | |
| 6,814,079 B2 | 11/2004 | Heaton et al. | |
| 6,824,533 B2 | 11/2004 | Risk, Jr. et al. | |
| 6,855,135 B2 | 2/2005 | Lockwood et al. | |
| 6,856,821 B2 | 2/2005 | Johnson | |
| 6,936,037 B2 | 8/2005 | Bubb et al. | |
| 6,951,553 B2 | 10/2005 | Bubb et al. | |
| 6,966,889 B2 | 11/2005 | Saab ......................... 604/96.01 | |
| 6,979,324 B2 | 12/2005 | Bybordi et al. | |
| 6,994,702 B2 | 2/2006 | Johnson | |
| 7,004,915 B2 | 2/2006 | Boynton et al. | |
| 7,022,113 B2 | 4/2006 | Lockwood et al. | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,735 B2 | 10/2006 | Weston | |
| 7,144,390 B1 | 12/2006 | Hannigan et al. | |

| | | | |
|---|---|---|---|
| 7,195,624 B2 | 3/2007 | Lockwood et al. | |
| 7,245,291 B2 | 7/2007 | Sharif et al. | |
| 7,276,051 B1 | 10/2007 | Henley et al. | |
| 7,338,482 B2 | 3/2008 | Lockwood et al. | 604/543 |
| 7,381,211 B2 | 6/2008 | Zamierowski | 606/215 |
| 7,422,576 B2 | 9/2008 | Boynton et al. | 607/104 |
| 7,524,286 B2 | 4/2009 | Johnson | 600/309 |
| 7,534,927 B2 | 5/2009 | Lockwood et al. | 602/46 |
| 2001/0029956 A1 | 10/2001 | Argenta et al. | |
| 2001/0034499 A1 | 10/2001 | Sessions et al. | |
| 2001/0043943 A1 | 11/2001 | Coffey | |
| 2001/0052681 A1 | 12/2001 | Deavila | 280/47.19 |
| 2002/0065494 A1 | 5/2002 | Lockwood et al. | |
| 2002/0077661 A1 | 6/2002 | Saadat | 606/221 |
| 2002/0082567 A1 | 6/2002 | Lockwood et al. | 604/313 |
| 2002/0082668 A1 | 6/2002 | Ingman | |
| 2002/0085952 A1 | 7/2002 | Ellingboe et al. | 422/45 |
| 2002/0115951 A1 | 8/2002 | Norstrem et al. | 602/27 |
| 2002/0115952 A1 | 8/2002 | Johnson et al. | |
| 2002/0120185 A1 | 8/2002 | Johnson | 600/345 |
| 2002/0143286 A1 | 10/2002 | Tumey | |
| 2002/0161317 A1 | 10/2002 | Risk et al. | |
| 2002/0183702 A1 | 12/2002 | Henley et al. | 604/305 |
| 2002/0193723 A1 | 12/2002 | Batdorf, Sr. et al. | |
| 2003/0032951 A1 | 2/2003 | Rittman, III et al. | |
| 2003/0077311 A1 | 4/2003 | Vyakarnam et al. | 435/41 |
| 2003/0093041 A1 | 5/2003 | Risk et al. | |
| 2003/0143352 A1 | 7/2003 | Yang et al. | 428/36.9 |
| 2003/0208149 A1 | 11/2003 | Coffey | |
| 2003/0219469 A1 | 11/2003 | Johnson et al. | |
| 2003/0225441 A1 | 12/2003 | Boynton et al. | |
| 2004/0030304 A1 | 2/2004 | Hunt et al. | |
| 2004/0039415 A1 | 2/2004 | Zamierowski | |
| 2004/0064111 A1 | 4/2004 | Lockwood et al. | |
| 2004/0167482 A1 | 8/2004 | Watson | |
| 2004/0225208 A1 | 11/2004 | Johnson | |
| 2004/0243073 A1 | 12/2004 | Lockwood et al. | |
| 2004/0249353 A1 | 12/2004 | Risk, Jr. et al. | |
| 2004/0260230 A1 | 12/2004 | Randolph | |
| 2005/0004534 A1 | 1/2005 | Lockwood et al. | |
| 2005/0010153 A1 | 1/2005 | Lockwood et al. | |
| 2005/0033197 A1* | 2/2005 | Cottler | 600/573 |
| 2005/0065484 A1 | 3/2005 | Watson, Jr. | |
| 2005/0070858 A1 | 3/2005 | Lockwood et al. | |
| 2005/0085795 A1 | 4/2005 | Lockwood et al. | |
| 2005/0090787 A1 | 4/2005 | Risk et al. | |
| 2005/0131327 A1 | 6/2005 | Lockwood et al. | |
| 2005/0177190 A1 | 8/2005 | Zamierowski | |
| 2005/0182445 A1 | 8/2005 | Zamierowski | |
| 2005/0182446 A1 | 8/2005 | DeSantis | 606/222 |
| 2005/0234485 A1 | 10/2005 | Seegert et al. | |
| 2005/0234510 A1 | 10/2005 | Zamierowski | |
| 2005/0240220 A1 | 10/2005 | Zamierowski | |
| 2005/0283105 A1 | 12/2005 | Heaton et al. | |
| 2006/0015087 A1 | 1/2006 | Risk, Jr. et al. | |
| 2006/0029650 A1 | 2/2006 | Coffey | |
| 2006/0029675 A1 | 2/2006 | Ginther | |
| 2006/0041247 A1 | 2/2006 | Petrosenko et al. | |
| 2006/0079852 A1 | 4/2006 | Bubb et al. | |
| 2006/0129137 A1 | 6/2006 | Lockwood et al. | |
| 2006/0149170 A1 | 7/2006 | Boynton et al. | |
| 2006/0149171 A1 | 7/2006 | Vogel et al. | |
| 2006/0173253 A1 | 8/2006 | Ganapathy et al. | |
| 2006/0189910 A1 | 8/2006 | Johnson et al. | |
| 2006/0213527 A1 | 9/2006 | Argenta et al. | |
| 2007/0005028 A1 | 1/2007 | Risk, Jr. et al. | |
| 2007/0014837 A1 | 1/2007 | Johnson et al. | |
| 2007/0021697 A1 | 1/2007 | Ginther et al. | |
| 2007/0021698 A1 | 1/2007 | Fleischmann | |
| 2007/0032778 A1 | 2/2007 | Heaton et al. | |
| 2007/0038172 A1 | 2/2007 | Zamierowski | |
| 2007/0156104 A1 | 7/2007 | Lockwood et al. | |
| 2007/0233022 A1 | 10/2007 | Henley et al. | 604/304 |
| 2009/0082740 A1 | 3/2009 | Lockwood et al. | 602/41 |

FOREIGN PATENT DOCUMENTS

| | | |
|---|---|---|
| AU | 745271 | 4/1999 |
| AU | 755496 | 2/2002 |
| CA | 1127488 | 7/1982 |
| CA | 2005436 | 6/1990 |
| CA | 2303085 | 3/1999 |
| DE | 372727 | 3/1923 |
| DE | 2640413 | 3/1978 |
| DE | 28 09 828 A1 | 9/1978 |
| DE | 3102674 A1 | 9/1982 |
| DE | 3539533 A1 | 5/1987 |
| DE | 4012232 | 10/1991 |
| DE | 4111122 A1 | 4/1993 |
| DE | 4306478 A1 | 9/1994 |
| DE | 29504378 U1 | 10/1995 |
| DE | 29715634 | 11/1997 |
| DE | 19722075 C1 | 10/1998 |
| DK | 64055 | 10/1945 |
| EP | 0 100 148 A1 | 2/1984 |
| EP | 0117632 A2 | 9/1984 |
| EP | 0 161 865 A2 | 11/1985 |
| EP | 0 358 302 A2 | 3/1990 |
| EP | 0424165 A1 | 4/1991 |
| EP | 0485657 A1 | 5/1992 |
| EP | 0547496 A1 | 6/1993 |
| EP | 0853 950 A1 | 7/1998 |
| EP | 0 777 504 B1 | 10/1998 |
| EP | 0 880 953 A2 | 12/1998 |
| EP | 1 088 569 A2 | 4/2001 |
| EP | 1100574 | 5/2001 |
| EP | 1 190 732 A1 | 3/2002 |
| EP | 1 018 967 B1 | 8/2004 |
| EP | 1726276 A2 | 11/2006 |
| FR | 500253 | 3/1920 |
| FR | 1303238 | 7/1962 |
| GB | 3090 | 0/1902 |
| GB | 641061 | 8/1950 |
| GB | 692578 | 6/1953 |
| GB | 1549756 | 8/1979 |
| GB | 1584772 | 2/1981 |
| GB | 2195255 A | 4/1988 |
| GB | 2197789 A | 6/1988 |
| GB | 2220357 A | 1/1990 |
| GB | 2235877 A | 3/1991 |
| GB | 2307180 A | 5/1997 |
| GB | 2329127 A | 3/1999 |
| GB | 2333965 A | 8/1999 |
| GB | 2336546 A | 10/1999 |
| GB | 2342584 A | 4/2000 |
| GB | 2344531 A | 6/2000 |
| GB | 2351025 A | 12/2000 |
| GB | 2356148 | 5/2001 |
| HU | 199304 | 1/1989 |
| HU | 51150 | 4/1990 |
| HU | 2005557 B | 4/1990 |
| HU | P9006526 | 1/1993 |
| HU | P9302966 | 7/1996 |
| HU | 76351 | 8/1997 |
| HU | 215563 B | 8/1997 |
| HU | 1666 | 12/1999 |
| JP | 4-129536 | 4/1992 |
| JP | 06327761 | 11/1994 |
| SE | 84485 | 10/1935 |
| SG | 71559 | 4/2002 |
| SU | 587941 | 1/1978 |
| SU | 1268175 A1 | 11/1986 |
| WO | WO 80/02182 | 10/1980 |
| WO | WO 87/04626 | 8/1987 |
| WO | WO 89/04158 | 5/1989 |
| WO | WO 90/10424 | 9/1990 |

| | | |
|---|---|---|
| WO | WO 90/11795 | 10/1990 |
| WO | WO 91/00718 | 1/1991 |
| WO | WO9108793 | 6/1991 |
| WO | WO 91/16030 | 10/1991 |
| WO | WO9212750 | 8/1992 |
| WO | WO92/19313 | 11/1992 |
| WO | WO 92/20299 | 11/1992 |
| WO | WO 93/09715 A1 * | 5/1993 |
| WO | WO 93/09727 | 5/1993 |
| WO | WO 94/00090 | 1/1994 |
| WO | WO 94/20041 | 9/1994 |
| WO | WO 96/05873 | 2/1996 |
| WO | WO9605873 A1 | 2/1996 |
| WO | WO 96/15745 | 5/1996 |
| WO | WO97/18007 | 5/1997 |
| WO | 98/02205 A | 1/1998 |
| WO | WO98/38944 A1 | 9/1998 |
| WO | WO99/01173 A1 | 1/1999 |
| WO | WO 99/13793 | 3/1999 |
| WO | WO9923990 | 5/1999 |
| WO | WO99/59816 A1 | 11/1999 |
| WO | WO 00/07653 | 2/2000 |
| WO | WO 00/15277 | 3/2000 |
| WO | WO 00/21586 | 4/2000 |
| WO | WO0021586 A1 | 4/2000 |
| WO | 00/28890 A | 5/2000 |
| WO | WO 00/26100 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 A1 | 5/2001 |
| WO | WO 01/37922 A2 | 5/2001 |
| WO | WO 01/49233 A1 | 7/2001 |
| WO | WO 01/85248 A1 | 11/2001 |
| WO | WO 01/89431 | 11/2001 |
| WO | WO01/89431 A1 | 11/2001 |
| WO | WO/0185248 A1 | 11/2001 |
| WO | WO 02/38091 A1 * | 5/2002 |
| WO | WO0238091 | 5/2002 |
| WO | WO 02/43634 | 6/2002 |
| WO | WO03/005943 A2 | 1/2003 |
| WO | WO03/045492 A1 | 6/2003 |
| WO | WO 03/057071 | 7/2003 |
| WO | WO 03/057307 | 7/2003 |
| WO | WO 03/101508 | 12/2003 |

OTHER PUBLICATIONS

Davydov, et al., Khirurgila, Jun. 1990—"Pathogenic Mechanism of the Effect of Vacuum Therapy on the Course of the Wound Process" (English translation by R. McElroy Translation Co., Austin, Texas.

Davydov, et al., Vestn. Khir., Nov. 1986—"Vacuum Therapy in the Treatment of Suppurative Lactation Mastitis" (English translation by R. McElroy Tranlations Co., Austin, Texas).

Davydov, et al., Vestn. Khir., Oct. 1988—"Bacteriological and Cytological Evaluation of the Vacuum Therapy of Suppurative Wounds"(English translation by R. McElroy Translation Co., Austin, Texas).

Davydov, et al., Vestn. Khir., Mar. 1990—"Basis of the Use of Forced Early Secondary Suture in the Treatment of Suppurative Wounds by the Vacuum Therapy Method" (English translation by R. McElroy Translation Co., Austin, Texas).

Mirazimov, et al., Ortop Travmatol Protez., Oct. 1996—"Free Skin Graft of the Foot with Preparation of the Wound Surface by Vacuum Treatment" (English translation by R. McElroy Translation Co., Austin Texas).

Borzov, et al., Vestn. Dermatol. Venerol., Aug. 1965—"Vacuum, Therapy of Some Skin Diseases" (English translation by R. McElroy Translation Co., Austin, Texas).

Jeter, et al., Chronic Wound Care; 27: pp. 240-246—"Managing Draining Wounds and Fistulae: New and Established Methods".

Mulder, et al., Wound Healing Publications 1991—"Clinicians' Pocket Guide to Chronic Wound Repair".

Valenta, AIN Apr. 1994; pp. 44-45—"Using the Vacuum Dressing Alternative for Difficult Wounds".

Wolthuis, et al., Physiological Reviews Jul. 1974; vol. 54, No. 3, pp. 566-595—"Physiological Effects of Locally Applied Reduced Pressure in Man".

Fleischmann, WundForum Spezial IHW 1994; pp. 54-55—"Vacuum Sealing for Treatment of Problematical Wounds" (English translation provided).

Bucalo, et al., Wound Repair and Regeneration; Jul.-Sep. 1993; pp. 181-186—"Inhibition of Cell Proliferation by Chronic Wound Fluid".

Olenius, et al., Plastic and Reconstructive Surgery Feb. 1993: pp. 213-215—"Mitotic Activity in Expanded Human Skin".

Viljanto, et al., Br. J. Surg. 1976; vol. 63: pp. 427-430—"Local Hyperalimentation of Open Wounds".

Dunlop, et al., Br. J. Surg. May 1990; vol. 77: pp. 562-563—"Vacuum Drainage of Groin Wounds after Vascular Surgery: A Controlled Trial".

Comment-Ruckley et al., Apr. 1991, pp. 505-506 on "Vacuum Drainage of Groin Wounds after Vascular Surgery".

Landis, et al. Alternate Suction and Pressure, pp. 925-961—"The Effects of Alternative Suction and Pressure on Blood Flow to the Lower Extremities".

Morykwas, et al., Extracellular Matrix and Healing 1993; pp. 800—"Use of Negative Pressure to Increase the Rate of Granulation Tissue Formation in Chronic Open Wounds".

Svedman, et al.. Annals of Plastic Surgery Aug. 1986; vol. 17, No. 2: pp. 125-133—"A Dressing System Providing Fluid Supply and Suction Drainage Used for Continuous or Intermittent Irrigation".

Schneider, et al., Plastic and Reconstructive Surgery Sep. 1998, pp. 1195-1198—"A New and Reliable Method of Securing Skin Grafts to the Difficult Recipient Bed".

Morykwas, et al., www.sma.org/soa/jsoawt97—"Nonsurgical Modalities to Enhance Healing and Care of Soft Tissue Wounds"; Feb. 11, 1999; 16 pages.

Chariker, et al., Contemporary Surgery Jun. 1989; vol. 34: pp. 59-63—"Effective Management of Incisional and Cutaneous Fistulae with Closed Suction Wound Drainage".

Tittel, et al., Eingag und Annahme des Manuskripts Jan. 7, 1987; pp. 104-107—"New Standards in Postoperative Wound Drainage".

Genecov, et al., Annals of Plastic Surgery Mar. 1998; vol. 40, No. 3: pp. 219-225—"A Controlled Subatmosheric Pressure Dressing Increases the Rate of Skin Graft Donor Site Reepithelialization".

Morykwas, et al., Annals of Plastic Surgery Jun. 1997; vol. 38, No. 6: pp. 553-562—"Vacuum-Assisted Closure: A New Method for Wound Control and Treatment: Animal Studies and Basic Foundation".

Argenta, et al., Annals of Plastic Surgery Jun. 1997; vol. 38, No. 6: pp. 563-577—"Vacuum-Assisted Closure: A New Method for Wound Control and Treatment: Clinical Experience".

Patent Application and Drawings—"Method of Treating Tissue Damage and Apparatus for Same", consisting of 28 pages.

Patent Application and Drawings—"The Enhancement of Wound Healing and Flap Survival by a New Negative Pressure Device", Argenta et al., consisting of 30 pages.

Nakayama, et al., Ann Plast Surg. May 1991; vol. 26, No. 5: pp. 499-502—"A New Dressing Method for Free Skin Grafting in Hands".

Medical Industry Week—article "KCI Offers New Treatment for Non-Healing Wounds"; 1 page.

Nakayama et al., Plast. Reconstr. Surg., Dec. 1990.; vol. 86, No. 6; pp. 1216-1219—"A New Method for the Dressing of Free Skin Grafts".

Sames, Br. Med. J., Nov. 5, 1977; vol. 2, No. 6096: 1123—"Sealing of Wounds with Vacuum Drainage".

Fleishmann, et al., Unfallchirurg 1993; 96:488-492—"Vacuum Sealing for Treatment of Soft Tissue Injury in Open Fractures" (English translation of the Summary provided).
Teder, et al., J. Invest. Surg. 1990; vol. 3: pp. 399-407—"Continuous Wound Irrigation in the Pig".
Wood, et al., Br. J. of Surg. 1977; vol. 64: pp. 554-557—"Foam Elastomer Dressing in the Management of Open Granulating Wounds, Experience with 250 Patients".
Neumann, et al., J. of Biomed. Materials Research 1981, vol. 15: pp. 9-18—"Gelatin-Based Sprayable Foam as a Skin Substitute".
Kostluchenok et al., Vestn. Khir. Sep. 1986—"Vacuum Treatment in the Surgical Treatment of Suppurative Wounds" (English translation by R. McElroy Translation Co., Austin, Texas).
Lundvall, et al., Acta Physiol. Scand. 1989, vol. 136: pp. 403-409—"Transmission of Externally Applied Negative Pressure to the Underlying Tissue. A Study on the Upper Arm of Man".
Brochure—Aeros—Instavac Aspirator; 1 page.
Brochure—Pleur-evac Adult-Pediatric-Non-Metered Disposable "3-Bottle" Unit, A-4000; 6 pages.
Brochure—Hiblow Air Pump; 1 page.
Brochure—Aeros—Care-E-Vac; 2 pages.
One page brochure—Aeros—MoblvacII.
Brochure/Instruction Manual—Creative Medical Laboratories, Inc.—TUGS (Transportable Universal Gradient Suction) System.
Brochure—Wells Johnson Company—Point 5 Aspirator; 2 pages.
Brochure—Microtek Heritage, Inc.—the Wound-Evac ET, Closed Wound Suction System; 4 pages.
Brochure—KCI—The V.A.C. (Vacuum Assisted Closure), Nov. 5, 1998; 7 pages.
Brochure—Augustine Medical, Warm-Up Active Wound Therapy Wound Covers, 1999; 3 pages.
Brochure—Series 55—Emerson Post-Operative Suction Pumps; 1 page.
Brochure—Emerson Transport Suction Unit; 1 page.
U.S. Appl. No. 6,216,701, filed Apr. 17, 2001, Heaton et al.
International Search Report for WO 03/045492A1, Lockwood et al., Jun. 2003.
Abdullah, BJJ, JHK Coll Radio1, Feb. 21, 2001; vol. 4, pp. 272-273—"A new Method for Fixation of Drainage Catheters".
European Search Report from EP 08 01 0957 dated Aug. 27, 2008.
Oosterbroek, R.E. et al., "A Micromachined Pressure/Flow-sensor" (Abstract only), http://www.ingentaconnect.com/content/els/09244247/1999/00000077/00000003/art00188, Sensors and Actuators A: vol. 77, No. 3, Nov. 2, 1999.
Office Action dated Apr. 15, 2008 relating to Application Serial No. 10/885,431, filed Jul. 6, 2004.
"Jump-Start Wound Healing with Oasis," Wounds, Special Supplement, 13(2):1-28, 2001.
"Oasis™ Wound Dressing," SIS™ Technology, pp. 1-4, Sep. 2001.
"Surgisis™ Soft-Tissue Graft," SIS™ Technology, pp. 1-4, Sep. 2001.
Arnljots and Svedman, "Irrigation Treatment in Split-Thickness Skin Grafting of Intractable Leg Ulcers," Scand J. Plast Reconstr. Surg., 19(2):211-213, 1985.
Bagautdinov, "Variant of external vacuum aspiration in the treatment of purulent diseases of soft tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
Blackburn II et al.; "Negative-pressure dressings as a bolster for skin grafts," Annals of Plastic Surgery, 40(5):453-457, 1998.
Brochure —"Cavi-Care," Smith & Nephew, 2000.
Brochure —Healthpoint® Oasis® Wound Matrix, Cook Biotech Incorporated, 2003.
Chinn and Burns, "Closed wound suction drainage," The Journal of Foot Surgery, 24(1):76-81, 1985.
Dattilo, Jr. et al.; "Medical textiles: application of an absorbable barbed bi-directional surgical suture"; Journal of Textile and Apparel, Technology and Management, 2(2):1-5, 2002.
Davydov et al., "Concepts for the clinical-biological management of the wound process in the treatment of purulent wounds by means of vacuum therapy," Vestnik Khirurgi, pp. 132-136 (and 8 page English translation thereof), Jul. 1980.

Egnell Minor, Instruction Book, First Edition, 300, 7502, pp. 24, Feb. 1975.
Egnell Minor: Addition to the Users Manual Concerning Overflow Protection —Concerns all Egnell Pumps, Feb. 3, 1983, pp. 2.
Fourth SIS-ECM Symposium, Phoenix, Arizona, Dec. 6-7, 2002.
Greer et al., "The use of subatmospheric pressure dressing therapy to close lymphocutaneous fistulas of the groin," British Journal of Plastic Surgery, 53(6):484-487, 2000.
Johnson, "An improved technique for skin graft placement using a suction drain," Surgery, Gynecology, and Obstetrics, 159(6):584-585, 1984.
Kinetic Concepts, Inc., Form 10-K —Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," PR Newswire, 2000.
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Letsou et al., "Stimulation of adenylate cyclase activity in cultured endothelial cells subjected to cyclic stretch," Journal of Cardiovascular Surgery, 31:634-639, 1990.
Letter and Memo reporting Office Action issued in Mexican Application No. PA/a/2001/001124, mailed Jul. 13, 2004.
Masters, "Reliable, inexpensive and simple suction dressings," Letter to the Editor, British Journal of Plastic Surgery, Elsevier Science/The British Association of Plastic Surgeons, UK, 51(3):267, 1998.
McCarty, "Cook Incorporated forms dedicated tissue engineered products group," Cook® Online, News and Media Information, 2000.
Mendez-Eastman, "When wounds won't heal," RN, 61(1):20-24, 1998.
Meyer and V. Schmieden, Bier's Hyperemic Treatment in Surgery, Medicine, and the Specialties: A Manual of Its Practical Application, (W.B. Saunders Co., Philadelphia, PA. 1909), pp. 17-25, 44-64, 90-96, 167-170, and 210-211.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.

Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.
Office Action issued in U.S. Appl. No. 09/994,537, mailed Jun. 30, 2003.
Office Action issued in U.S. Appl. No. 10/144,504, mailed May 15, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Dec. 20, 2007.
Office Action issued in U.S. Appl. No. 10/509,137, mailed Jun. 3, 2009.
Office Action issued in U.S. Appl. No. 10/509,137, mailed Jun. 22, 2007.
Office Action issued in U.S. Appl No. 10/509,137, mailed Jan. 10, 2007.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 10, 2007.
Office Action issued in U.S. Appl. No. 10/524,957, mailed Aug. 3, 2009.
Office Action issued in U.S. Appl. No. 10/524,957, mailed Sep. 30, 2008.
Office Action issued in U.S. Appl. No. 10/664,535, mailed Apr. 17, 2008.
Office Action issued in U.S. Appl. No. 10/664,535, mailed Apr. 2, 2007.
Office Action issued in U.S. Appl. No. 10/664,535, mailed Mar. 1, 2006.
Office Action issued in U.S. Appl. No. 10/664,535, mailed Oct. 26, 2007.
Office Action issued in U.S. Appl. No. 10/664,535, mailed Oct. 16, 2006.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Mar. 22, 2007.
Office Action issued in U.S. Appl. No. 11/051,283, mailed Oct. 17, 2008.
Office Action issued in U.S. Appl. No. 11/051,283, mailed Sep. 7, 2007.
Office Action issued in U.S. Appl. No. 11/051,283, mailed Sep. 29, 2006.
Office Action issued in U.S. Appl. No. 11/051,283, mailed Sep. 7, 2005.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 13, 2007.
Office Action issued in U.S. Appl. No. 11/230,988, mailed Mar. 26, 2008.
Office Action issued in U.S. Appl. No. 11/230,988, mailed Oct. 3, 2008.
Office Action issued in U.S. Appl. No. 11/230,988, mailed Sep. 28, 2006.
Office Action issued in U.S. Appl. No. 11/230,988, mailed Sep. 10, 2007.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Application No. 11/347,073, mailed Apr. 1, 2008.
Office Action issued in U.S. Appl. No. 11/515,983, mailed May 11, 2009.
Office Action issued in U.S. Appl. No. 11/684,989, mailed Jul. 7, 2009.
Office Action issued in U.S. Appl. No. 11/684,989, mailed Nov. 18, 2008.
Office Action issued in U.S. Appl. No. 11/761,066, mailed Dec. 13, 2007.
Office Action issued in U.S. Appl. No. 11/761,066, mailed Jun. 2, 2009.

Office Action issued in U.S. Appl. No. 11/761,066, mailed Oct. 28, 2008.
Office Action issued in U.S. Appl. No. 11/761,066, mailed Sep. 25, 2007.
Orringer et al., "Management of wounds in patients with complex enterocutaneous fistulas," *Surgery, Gynecology & Obstetrics*, 165:79-80, 1987.
PCT Declaration of Non-Establishment of International Search Report issued in International Application No. PCT/US03/17099, mailed Nov. 7, 2003.
PCT International Preliminary Examination Report issued in International Application No. PCT/GB1996/02802, mailed Jan. 15, 1998.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Examination Report issued in International Application No. PCT/US2001/44194, mailed Dec. 3, 2003.
PCT International Search Report issued in International Application No. PCT/GB1995/01983, mailed Nov. 23, 1995.
PCT International Search Report issued in International Application No. PCT/GB1996/02802, mailed Apr. 29, 1997.
PCT International Search Report issued in International Application No. PCT/GB1998/02713, mailed Jan. 8, 1999.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/37814, mailed Apr. 7, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/GB1996/02802, mailed Sep. 3, 1997.
PCT Written Opinion issued in International Application No. PCT/GB1998/02713, mailed Jun. 8, 1999.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus, First Edition (v 1.3.1), 2007.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).
Schein et al., "The 'Sandwich Technique' in the management of the open abdomen," *British Journal of Surgery*, 73:369-370, 1986.
Search Report issued in Hungarian Application No. P0103545, mailed Oct. 29, 2001.
Search Report issued in Hungarian Application No. P0500055, mailed May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary Search Report issued in European Application No. 02794388.5, mailed Jun. 16, 2009.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 07001838.7, mailed Mar. 5, 2007.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Tennant, "The use of hypermia in the postoperative treatment of lesions of the extremities and thorax,"*Journal of the American Medical Association*, 64:1548-1549, 1915.
Tribble, "An improved sump drain-irrigation device of simple construction," *Archives of Surgery*, 105(3):511-513, 1972.
Wooding-Scott et al., "No wound is too big for resourceful nurses," *RN*, pp. 22-25, 1988.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and copy and certified translation), 1986.

\* cited by examiner

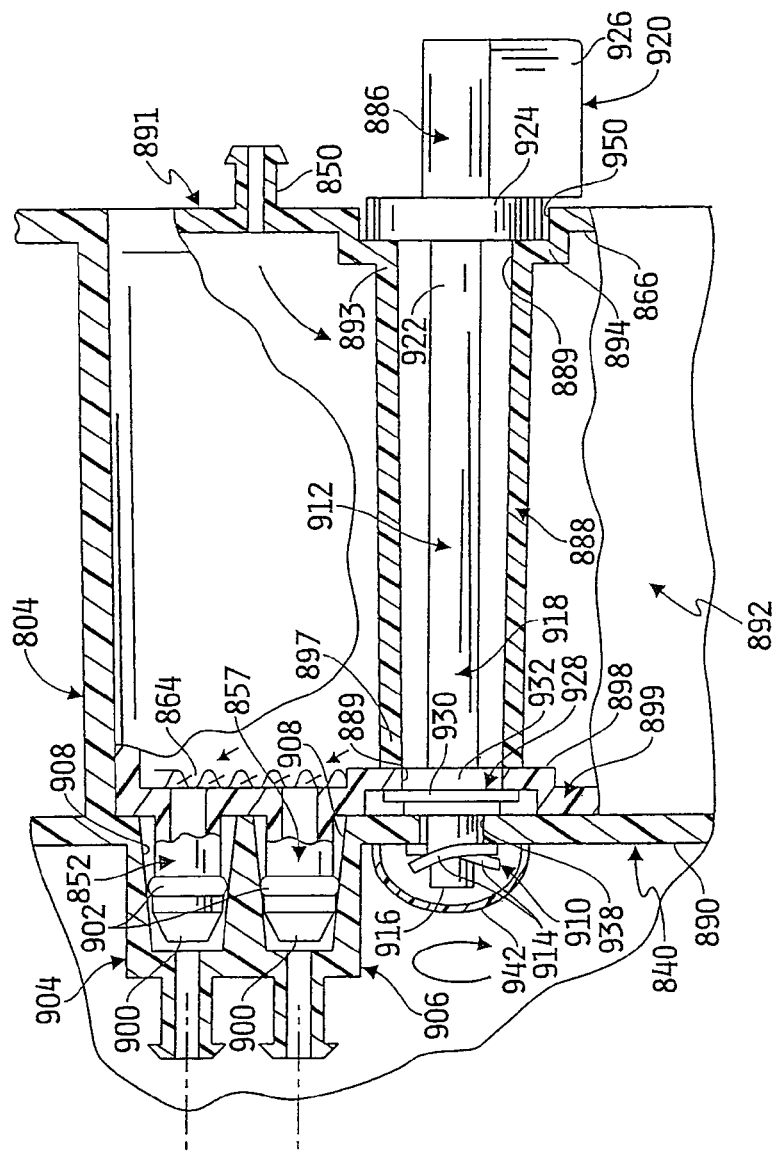
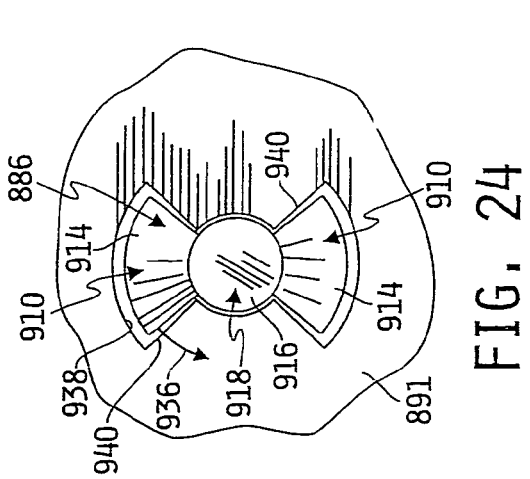
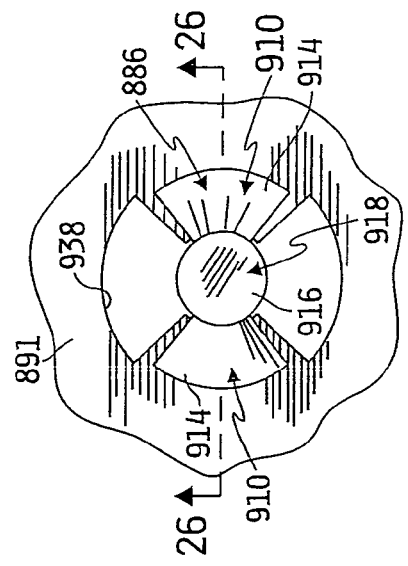

WOUND TREATMENT APPARATUS

RELATED APPLICATION

This disclosure is a division of U.S. Ser. No. 10/159,720, filed May 31, 2002, which is hereby incorporated herein by reference. U.S. Ser. No. 10/159,720 is U.S. Pat. No. 6,824,533, issued Nov. 30, 2004. U.S. Ser. No. 10/159,720 is a continuation-in-part of U.S. application Ser. No. 09/725,666, which was filed Nov. 29, 2000 and which is hereby incorporated by reference herein. U.S. Ser. No. 09/725,666 is U.S. Pat. No. 6,755,807, issued Jun. 29, 2004. U.S. Ser. No. 09/725,666 is a regular utility patent application claiming the benefit of the filing date of U.S. Provisional Application Ser. No. 60/167,753, filed on Nov. 29, 1999.

TECHNICAL FIELD

The present disclosure relates to wound treatment apparatus for use with vacuum bandages of the type that dispenses fluid to a wound and draws fluid away from the wound.

BACKGROUND AND SUMMARY

Medical professionals, such as nurses and doctors, routinely treat patients having surface wounds of varying size, shape, and severity. It is known that controlling the topical atmosphere adjacent a wound can enhance the healing process. For example, by applying medicinal agents or even water over a wound, dirt and bacteria are either killed or washed away, thereby promoting healing. In addition, applying a negative pressure or vacuum to a wound draws out exudate, which might contain dirt and bacteria, from the wound to further promote healing.

Conventional treatment of a surface wound involves placement of a packing or dressing material, such as cotton, gauze, or other bandage-like material directly in contact with the patient's wound. Often there is a need to change the dressing material frequently because it becomes saturated with exudate discharged from the wound. Some dressings include an apparatus attached thereto for applying a vacuum through the bandage to the wound to draw exudate and promote healing.

According to the present disclosure, a control unit is adapted for use with a vacuum wound bandage. The control unit comprises a control module to provide a negative pressure through the vacuum wound bandage and a canister having an interior region to collect waste material from the vacuum wound bandage and a latch to couple the canister to the control module. The latch extends through the interior region. Illustratively, the latch is operable to move the canister into sealing engagement with the control module. Further illustratively, the canister has a sleeve positioned within the interior region, and a portion of the latch is positioned within the sleeve.

According to another aspect of the disclosure, the control unit comprises a vacuum source to provide a desired negative pressure through the vacuum wound bandage to treat the wound, a pressure sensor, and a canister. The canister has a chamber to collect waste material from the vacuum bandage, an inlet port to introduce waste material from the vacuum bandage into the chamber, an outlet port to communicate with the chamber and the vacuum source, and a pressure port to communicate with the chamber and the pressure sensor. The pressure port is positioned to allow the pressure sensor to sense the pressure within the chamber when the waste material within the chamber at least partially occludes the outlet port so as to prohibit the vacuum source from providing the desired negative pressure within the chamber.

According to another aspect of the disclosure, the control unit comprises a fluid source to irrigate the wound, a housing carrying the vacuum source and the fluid source, and a door movable relative to the housing between an opened position uncovering the fluid source and a closed position at least partially covering the fluid source. The control unit further comprises a latch coupled to the door for movement relative to the door between a latched position blocking movement of the door from its closed position to its opened position and a release position allowing the door to move between its closed position and its opened position. According to another aspect of the disclosure, the door has a mount supporting the fluid source.

Additional features and advantages of the apparatus will become apparent to those skilled in the art upon consideration of the following detailed descriptions exemplifying the best mode of carrying out the apparatus as presently perceived.

BRIEF DESCRIPTION OF THE DRAWINGS

The illustrative apparatus will be described hereinafter with reference to the attached drawings, which are given as non-limiting examples only, in which:

FIG. 1 is a perspective view of a wound treatment apparatus coupled to a bandage attached to a patient;

FIG. 2 is a block diagram of the wound treatment apparatus of FIG. 1;

FIG. 3 is a schematic diagram of the wound treatment apparatus of FIG. 1;

FIG. 4 is a side cross-sectional view of the wound treatment apparatus along the lines A-A of FIG. 1;

FIG. 5 is a schematic block diagram of the vacuum evacuating sub-system of the wound treatment apparatus of FIG. 1;

FIG. 6 is a cross-sectional view of a waste disposal canister of the wound treatment apparatus along the lines B-B of FIG. 1;

FIG. 7 is a partially exploded perspective view of the wound treatment apparatus of FIG. 1 with the waste canisters removed;

FIG. 8 is a perspective view of another embodiment of the wound treatment apparatus;

FIG. 9 is a side diagrammatic view of the vacuum bandage and portions of the wound treatment apparatus of FIG. 1;

FIG. 10 is a perspective view of the wound treatment apparatus of FIG. 1 with the waste canister removed;

FIG. 11 is a front elevational view of a waste canister;

FIG. 12 is a side elevational view of the waste canister of FIG. 11; and FIG. 13 is a top view of the waste canister of FIG. 11.

FIG. 14 is a perspective view of another wound treatment apparatus showing a pair of canisters arranged for insertion into respective receptacles formed in the sides of a housing of a control unit and showing a fluid source arranged for insertion into a receptacle formed in the front of the housing;

FIG. 15 is an enlarged elevation view of a latch for a door of the wound treatment apparatus of FIG. 14 showing the latch in a release position;

FIG. 16 is a view similar to FIG. 15 showing the latch in a latched position;

FIG. 17 is a fragmentary sectional view showing a syringe having a flange received by grooves of the door and the housing to retain a barrel of the syringe in place;

FIG. 23 is a side sectional view similar to FIG. 22 of the canister installed within the receptacle;

FIG. 24 is an enlarged elevation view of the interface between the latch and a wall of the receptacle showing lugs of the latch aligned with lug-receiving spaces of an aperture formed in the receptacle wall;

FIG. 25 is an enlarged elevation view, similar to FIG. 24, showing the lugs of the latch misaligned with the lug-receiving spaces of the aperture to retain the canister in the receptacle;

Corresponding reference characters indicate corresponding parts throughout the several views. The exemplification set out herein illustrates several embodiments of the apparatus, and such exemplification is not to be construed as limiting the scope of this disclosure in any manner.

DETAILED DESCRIPTION OF THE DRAWINGS

Figure 1:
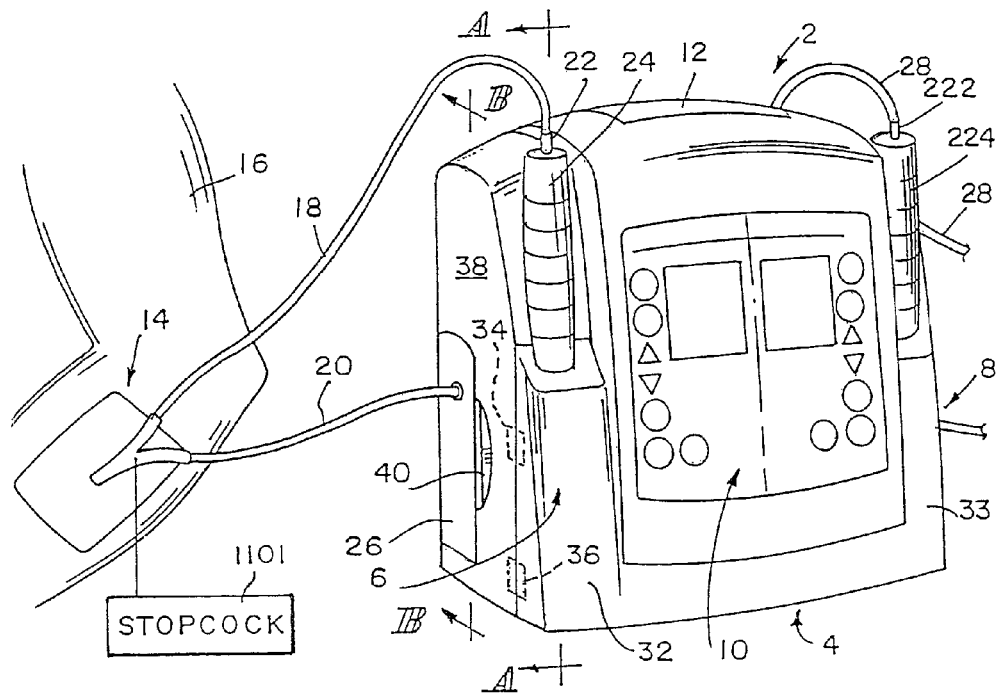

An embodiment of wound treatment apparatus 2 is shown in FIG. 1. Wound treatment apparatus 2 comprises a central unit housing 4, having wound treatment systems 6, 8 appended to each side of housing 4. A user interface 10 is shown positioned between each treatment system 6, 8. Central unit housing 4 is configured to be a portable unit allowing a caregiver to move housing 4 to wherever the patient is located and to close proximity to the wound or wounds. Housing 4 is shown having a handle portion 12 to assist the caregiver in moving housing 4. FIG. 1 also shows wound treatment system 6 coupled to a bandage 14 attached to a patient's leg 16. Dispensing and evacuating tubes 18, 20 are coupled to both bandage 14 and system 6. Specifically, dispensing tube 18 is coupled to a luer-lok port 22 extending from syringe 24. Syringe 24 is filled with a fluid, typically saline, that empties through tube 18 and into bandage 14, and ultimately onto a wound 300 positioned under bandage 14. (See also FIG. 9.) After contacting wound 300, the fluid and exudate from wound 300 are drawn from bandage 14 through evacuating tube 20 and into a waste canister 26 where it is collected. It is contemplated that the canister 26 can be discarded when filled and replaced with a new canister 26.

Apparatus 2 comprises a second system 8 on the opposite side of housing 4 from system 6. This configuration allows two wounds to be treated simultaneously with separate bandages, yet, under the control of a single housing 4. Second bandage 15, as part of system 8, is coupled to dispensing and evacuating tubes 28, 30, respectively, to perform the same functions as described for system 6. (See FIG. 2.) User interface 10 is provided to allow the caregiver to control either or both systems 6, 8, to dispense fluid from either or both syringes 24, 224, and to evacuate from either or both bandages 14, 15. It is contemplated that each wound treatment system 6, 8 will work independent of each other, thus, allowing the caregiver flexibility to apply an appropriate and, yet, possibly different level of treatment to each wound.

The arrangement of systems 6, 8 relative to user interface 10 on housing 4 allows convenient interaction between systems 6, 8 and the caregiver. For example, syringes 24, 224 are conveniently positioned on opposite sides of user interface 10. Each syringe is partially covered by doors 32, 33 on the front of housing 4. Each door 32, 33 swings outwardly about hinges 34, 36, allowing syringes 24, 224 to be removed and replaced. Similarly, waste canisters 26, 27 are each positioned in a cavity 9 provided on each side of housing 4. (See FIG. 7.) Each canister 26, 27 includes a grip portion 40 for convenient removal and replacement. Canisters 26, 27 are illustratively secured into each cavity by a friction fit. (See FIG. 6.) It is appreciated, however, that syringes 24, 224 can be secured to other locations on housing 4.

The portability of apparatus 2 allows a caregiver to position it near the patient in preparation for treatment wherever the patient is located. To prepare apparatus 2 for treatment, the caregiver secures syringes 24, 224, which contain fluid, to apparatus 2 in a manner described in greater detail below. The caregiver then couples tube 18 to port 22 and bandage 14, and tube 20 to bandage 14 and waste canister 26, for treatment of one wound. The caregiver then couples tube 28 to port 222 and bandage 15, and tube 21 to bandage 15 and waste canister 27, for treatment of a second wound. (See also FIG. 2.) The caregiver, through the use of user interface 10 can treat the patient by selectively irrigating the wounds with fluid and drawing exudate and the fluid from the wounds.

Figure 2:
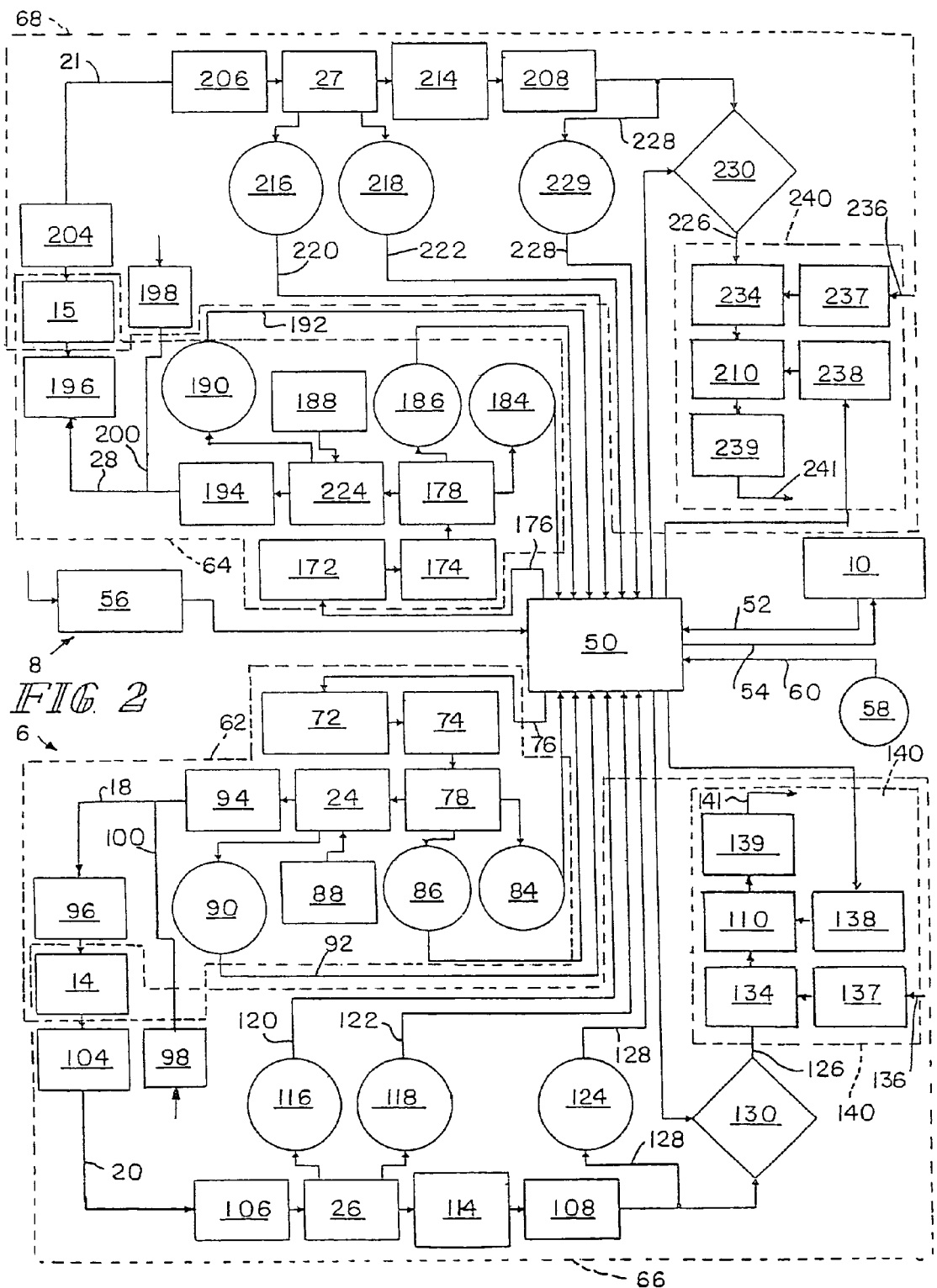

A diagram depicting how wound apparatus 2 operates is shown in FIG. 2. A controller 50 is provided in housing 4 and is an electronic control unit that controls apparatus 2. Controller 50 receives user input from and provides feedback to user interface 10 through lines 52, 54, respectively. It is contemplated that controller 50 will process information from both systems 6, 8, and provide appropriate and independent input to each system. Controller 50 also monitors the status of all various sensors, and provides input for the valves and motors, as discussed in further detail herein. Illustratively, user interface 10 is composed of a conventional graphic liquid crystal display (LCD) and a membrane switch panel.

A power supply 56 provides power to controller 50 and all the attendant systems in housing 4. Power supply 56 can be a conventional external wall socket supply (not shown), or be a battery pack supply (also not shown), or even be variations of both (e.g., a wall socket supply with a battery pack supply). Illustratively, power supply 56 is a medical grade power supply providing an output of about 65-watts and a voltage of about 12VDC. It is contemplated that the power supply can be configured for 120V/60 Hz or 220-240V/50 Hz depending on whether housing 4 is used in America or Europe. Illustratively, the battery power provides the device with power to operate for about 60 minutes without connection to an external power source. It is further contemplated that the batteries can be rechargeable, and store energy when the device is connected to an external wall socket.

An attitude sensor 58 is provided in communication with controller 50 through line 60. Attitude sensor 58 is, illustratively, a tilt switch which provides feedback to controller 50. If the switch is, illustratively, in the closed position, controller 50 will continue to operate, but if the switch opens, controller will shut systems 6, 8 down. For example, sensor 58 disables systems 6, 8 if housing 4 tilts at or greater than a predetermined amount, such as 45° from vertical in any direction.

It is contemplated that controller 50, user interface 10, power supply 56, and attitude sensor 58 are all common to and all operate with both systems 6, 8. Each system 6, 8 further comprises fluid dispensing and vacuum evacuating sub-systems 62, 64 and 66, 68. Fluid dispensing sub-system 62 comprises a syringe 24 having a plunger 70. (See also FIG. 4.) Syringe 24 is, illustratively, a standard 60-ml medical syringe utilizing a luer-lok port 22. Plunger 70 is a conventional plunger that extends into syringe 24 to dispense fluid through luer-lok port 22. A syringe drive motor 72 is, illustratively, a 12VDC brushless electric motor or stepper motor configured to provide rotational energy to a syringe drive 74. (See FIG. 4.) When a signal is sent from controller 50 along line 76 to syringe drive motor 72, motor 22 applies torque and angular velocity to syringe drive 74 which is, illustratively, a power screw 322. (See also FIG. 4.) Power screw 322 translates rotational movement of the syringe drive motor 72 into translational movement. The drive has a guide 80 to limit a plunger interface 78 to motion along one axis. In the illustrated embodiment, syringe drive 72 provides about 5.25 inches (13.3 cm) of travel of plunger interface 78, indicated by reference numeral 82, to evacuate the fluid contained in syringe 24. (See also FIG. 4.) Furthermore, syringe drive motor 72 and syringe drive 74, as a system, provide about 27 pounds of linear force at a velocity of 1.45 inches (3.7 cm) per second to the plunger interface 78. The resulting force created by the fluid exiting syringe 24 creates, illustratively, 4-PSIG to 6-PSIG positive pressure at wound 300.

A syringe home sensor 84 receives information from plunger interface 78, and provides feedback to controller 50 when syringe capture mechanism 88 reaches its home position 79. A syringe full travel sensor 86 determines when syringe 24 is fully evacuated by sensing when plunger interface 78 has reached fill travel. After sensor 86 has been activated, controller 50 resets plunger interface 78 to home position 79 once syringe 24 is removed.

Syringe capture mechanism 88 holds syringe 24 in place when the caregiver places syringe 24 in apparatus 2. (See also FIG. 4.) Capture mechanism 88 is also configured to allow the caregiver to release syringe 24 from apparatus 2 when it is empty. Capture mechanism 88 further includes a syringe sensor 90 that provides feedback to controller 50 through line 92 when syringe 24 is properly held in capture mechanism 88. Controller 50 prevents system 6 from operating if sensor 90 does not detect syringe 50 being properly held in capture mechanism 88.

Connectors 94, 96 are provided at opposed ends of dispensing tube 18. Either one or both connectors 94, 96, when closed, block flow from syringe 24 to bandage 14. Such connectors 94, 96 allow the patient to be disconnected from apparatus 2 without having to remove bandage 14 or even shut apparatus 2 down.

A manual port 98 is also attached to dispensing tube 18 by an auxiliary tube 100. Port 98 permits the caregiver to attach a dispensing container to the system to manually dispense fluid into bandage 14. It is appreciated, however, that port 98 is configured to be closed while no syringe is attached to maintain a closed system.

The syringe and drive are illustrated as one approach for providing a fluid source and a drive for irrigating a wound bed. It will be appreciated that containers other than syringes may be operated by a drive to expel irrigation fluid toward a wound surface. For example, any type of container of fluid may be squeezed or reduced in volume by a drive mechanism to expel fluid. Also, as discussed in connection with FIG. 8, a container may be held at an elevated position to provide head pressure for irrigation fluid.

Connectors 104, 106, similar to connectors 94, 96, are provided at opposed ends of evacuating tube 20. Either one or both connectors 104, 106, when closed, block flow from bandage 14 to waste canister 26. Such connectors 104, 106 also allow the patient to be disconnected from apparatus 2 without having to remove bandage 14 or having to shut down apparatus 2.

Waste canister sensors 116, 118 are engaged when waste container 26 is properly seated in apparatus 2. This prevents apparatus 2 from operating without canister 26 seated properly in apparatus 2. As depicted in FIG. 2, both sensors 116, 118 provide feedback to controller 50 through lines 120, 122, confirming to the caregiver that canister 26 is seated properly in apparatus 2.

In the illustrated embodiment, waste canister 26 is a disposable unit that "snaps into" side portion 38 of housing 4. (See also FIGS. 1 and 6.) Illustratively, canister 26 includes a window (not shown) to allow monitoring of the fluids. Illustratively, the fluid capacity of canister 26 is about 500-ml.

The illustrated embodiment of waste canister 26 further includes a hydrophobic filter 108 that is in communication with both evacuating tube 20 and vacuum pump 110. (See also FIG. 6.) Such filter 108 is configured to allow air, but not liquid, to pass. Accordingly, as fluid is drawn into canister 26, fluid is deposited into waste canister 26 while the vacuum continues through filter 108 and pump 110. Illustratively, filter 108 is a 1.0-micron hydrophobic filter fixed into rear wall 407 of canister 26. (See FIG. 6.) Hydrophobic filter 108 also serves as a canister full mechanism 114 or valve that shuts off the vacuum supply to the canister 26 when the fluid level exceeds the "full" level 420. Because hydrophobic filter 108 prevents fluid from passing, once fluid covers filter 108, vacuum is prevented from passing as well. The absence of any vacuum in the system will cause the system to shut down.

Figure 5:
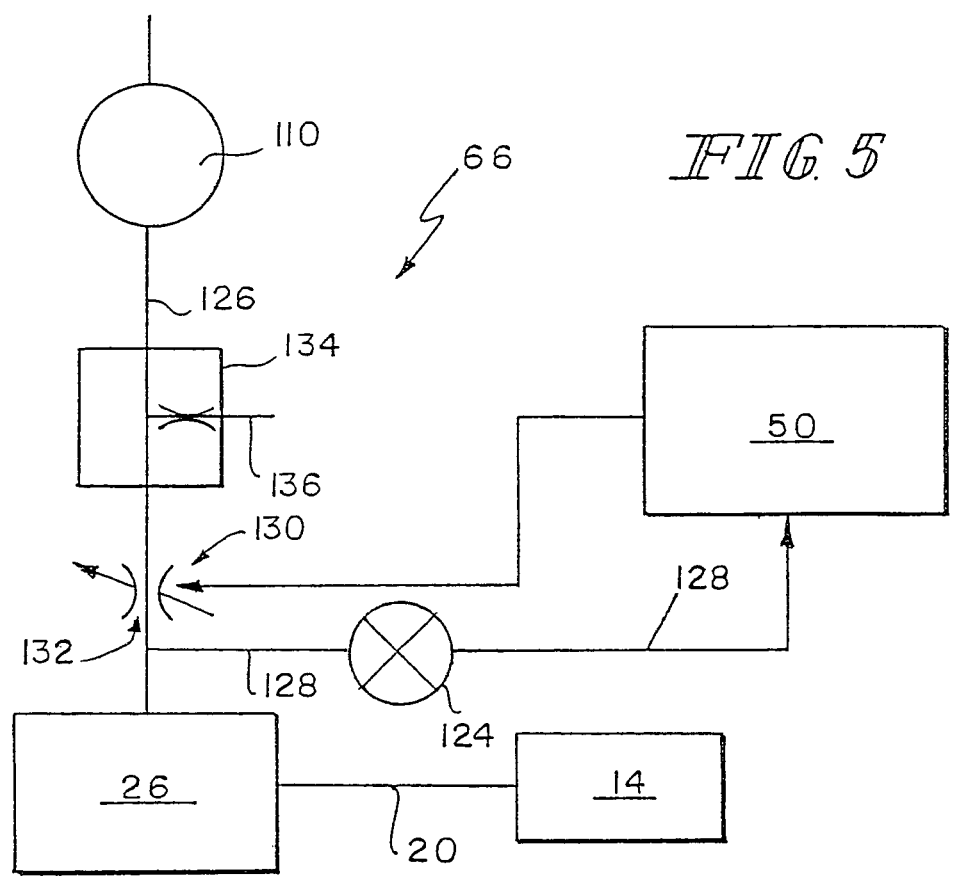

Vacuum pump 110 creates the negative pressure that is present through canister 26. For monitoring and controlling such negative pressure, the vacuum is present through several devices, including a vacuum pressure transducer 124. Transducer 124 is coupled to line 128, extending from canister 26. (See FIG. 5.) Transducer 124 measures the negative pressure that is present through canister 26. Transducer 124 then provides feedback to controller 50 through line 128. Controller 50 monitors the negative pressure by comparing the measured value from transducer 124 with the caregiver-defined value entered into controller 50 through user interface 10.

A proportional valve 130 is connected to line 126, through which the negative pressure is present, and which comprises a flow orifice 132. (See also FIG. 5.) Flow orifice 132 selectively dilates or constricts, thereby controlling the negative pressure level through sub-system 66. Specifically, controller 50 provides a signal input to proportional valve 130 based on the level of the vacuum pressure determined from feedback of transducer 124 and comparing that level to the caregiver-defined level. Orifice 132 then dilates or constricts, as necessary, to produce the appropriate level of negative pressure. Illustratively, proportional valve 130 is fully constricted or closed when receiving no signal from controller 50, and dilates or opens to allow an illustrative maximum of two liters per minute at 250-mmHg (4.83-PSIG) vacuum when the proper signal from controller 50 is applied.

A vacuum regulator 134 is provided in line 126 between proportional valve 130 and pump. 110 as a mechanical limit control for pump 110. Regulator 134 mechanically establishes a maximum level of negative pressure that is present in the system. Thus, vacuum pump 110 will not physically be able to draw a vacuum from bandage 14 beyond the maximum pressure. Illustratively, such maximum negative pressure or vacuum is 250-mmHg (4.83-PSIG). In addition, when proportional valve 130, pursuant to a signal from controller 50, creates a negative pressure less than the maximum negative pressure level, a port 136, coupled to regulator 134, opens so that pump 110 can draw more air to maintain a sufficient flow through pump 110, to prevent it from becoming damaged. A first air filter 137 is illustratively associated with port 136, between port 136 and pump 110, to filter particulates from the air prior to reaching pump 110. illustratively, filter 137 is constructed of glass microfibers with a filtration rating of 25 microns. A second filter 139 is associated with pump 110 and an outlet 141. Filter 139 serves as an exhaust muffler for the air evacuated from pump 110.

Vacuum pump 110 is, illustratively, a diaphragm-type compressor that flows about two liters per minute at 250-mmHg (4.83-PSIG) vacuum. Illustratively, vacuum pump 110 is mounted on the end of a single 12VDC brushless motor 138 to drive the pump. It is appreciated, however, that pump 110 can be of any other configuration, and mounted in any manner, so long as it draws a desired negative pressure through system 6. It is also contemplated that a vacuum pump external to the housing 4 may be a part of the control system. For example, most medical facilities have vacuum ports near where patients are treated, each of which is served by a system vacuum (suction) pump. It is contemplated, therefore, that the pump 110 in the housing 4 may be an appropriate fitting which is, in turn, connected to a facility vacuum pump to provide a vacuum source to the control system.

It is contemplated that port 136, filters 137, 139, electric motor 138, vacuum pump 110, and vacuum regulator 134 are all housed in a sound chamber 140. Illustratively, the interior of sound chamber 140 is lined with a damping foil like the 3M Company's damping foil number 2552, for example. Sound chamber 140 dampens vibration energy produced by these components, as well as assists in dissipating heat they generated.

As previously indicated, it is contemplated that controller 50, user interface 10, power supply 56, and attitude sensor 58 are common to, and operate with, both fluid dispensing and vacuum evacuating sub-systems 62, 64 and 66, 68. Providing a second independently operable set of sub-systems 64, 68 allows the caregiver to treat two wounds using a single apparatus 2. Accordingly, second fluid dispensing and evacuating sub-systems 64, 68 also shown in FIG. 2, comprise identical components as discussed regarding sub-systems 62, 66 and are labeled in a corresponding manner. For example, syringe motor drive 72 in sub-system 62 is identified as syringe motor drive 172 in sub-system 64, and a vacuum pump 110 in sub-system 66 is identified as vacuum pump 210 in sub-system 68.

Figure 3:
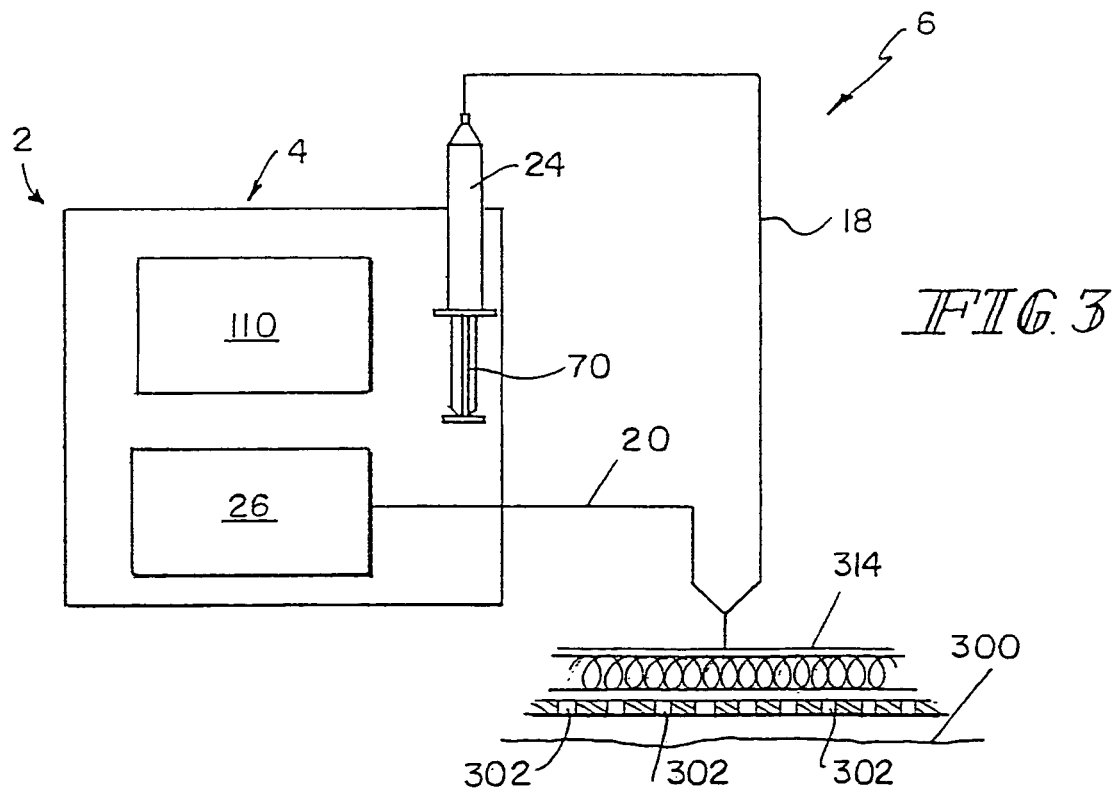

A schematic diagram of a portion of wound treatment apparatus 2 is shown in FIG. 3. Each system 6 and 8 is configured to operate in the same manner. Specifically, FIG. 3 depicts the operation of system 6. Movement of plunger 70 into syringe 24 causes fluid stored in syringe 24 to exit into tube 18 and into bandage 314 where it drains through orifices 302 onto wound 300. Vacuum 110 applies a negative pressure through waste canister 26 and bandage 314. Fluid and exudate are then drawn from wound 300 out through tube 20 and into canister 26. The hydrophobic filter 108, discussed in connection with FIG. 2, allows the vacuum to pass through waste canister 26, yet prevents any of the fluid from escaping, and depositing the fluid into pump 110.

Figure 4:
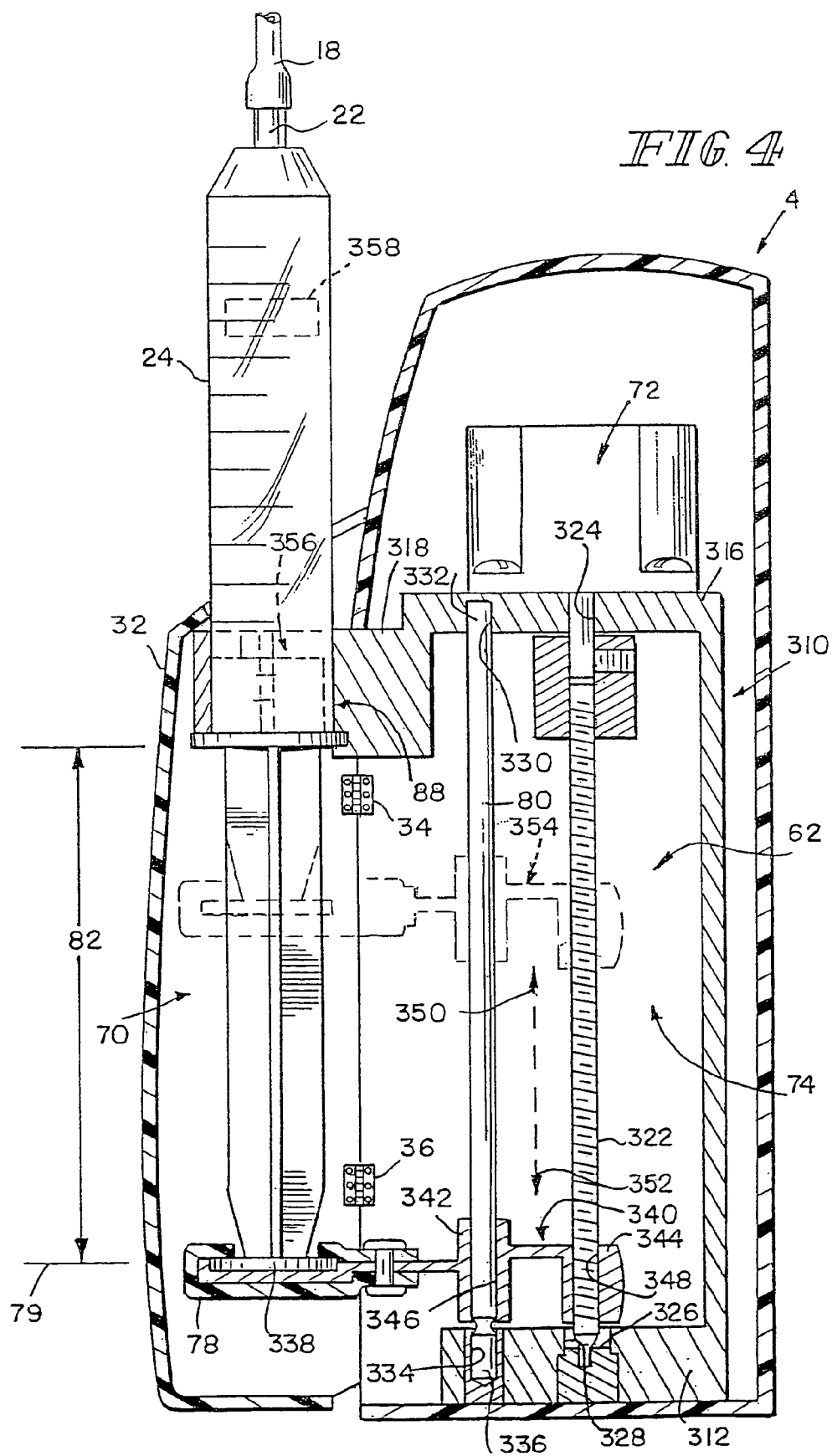

The mechanism for moving plunger 70 into syringe 24, part of fluid dispensing sub-system 62, is shown in cross-sectional form in FIG. 4. The illustrated embodiment includes sub-system 62 positioned within housing 4. Specifically, a bracket frame 310 serves as the skeletal structure for sub-system 62. Bracket 310 includes a base portion 312 with an upwardly extending structural member 314 appending from one end thereof. A support portion 316 extends outwardly from member 314, and is superposed above base portion 312. Extending from support portion 316 is syringe bracket 318. Syringe capture mechanism 88 is formed in bracket 318, and is configured to receive syringe 24, as previously discussed. Bracket 318 and capture mechanism 88 are configured to suspend syringe 24 with luer-lok port 22 directed upwardly. It is contemplated that capture mechanism 88 secures syringe 24 to bracket 318 by other means, including being friction-fitted, or secured with clips or bolts. To move plunger 70, syringe drive 74 and plunger interface 78 are coupled to frame 310. Plunger interface 78 captures plunger 70 and provides upward linear motion to evacuate syringe 24. Interface 78 provides a release mechanism for plunger 70 to remove syringe 24 at any position in the stroke.

Syringe drive 74 comprises syringe drive motor 72 and power screw 322. Power screw 322 is disposed through an aperture 324 in support portion 316, and is rotatably coupled to motor 72. It is appreciated that motor 72 can be a stepper or electric motor, for example. The lower end 326 of power screw 322 is positioned within a bearing cavity 328 within which power screw 322 rotates. Spaced in parallel to power screw 322 is guide 80. Guide 80 is received in an aperture 330, also disposed in support portion 316 at its upper end 332, and is received in cavity 334 at its lower end 336. Plunger interface 78 is configured to receive cap 338 of plunger 70, and is coupled to a dual coupler 340. Dual coupler 340 comprises two blocks 342, 344, each having bores 346, 348 disposed, respectively, there through. In the illustrated embodiment, bore 346 has a smooth surface and is configured to receive guide 80. In contrast, bore 348 has a threaded surface and is configured to cooperate with threads on power screw 322. Coupler 340 is movable upwardly and downwardly in directions 350, 352. A hatched outline version of coupling 340, indicated by reference numeral 354, is shown depicting plunger interface 78 and plunger 70 moving upwardly in direction 350. As shown in FIG. 4, as plunger 70 is moved upwardly, head 356 is also moved upwardly, reducing the available space in syringe 24, thus, displacing any fluid in syringe 24 out of luer-lock port 22, thereby dispensing the fluid into tube 18 and into bandage 14. The movement of cap 356 is depicted by the position of cap 356 in hatched lines moved to an upper position indicated by reference numeral 358.

Figure 6:
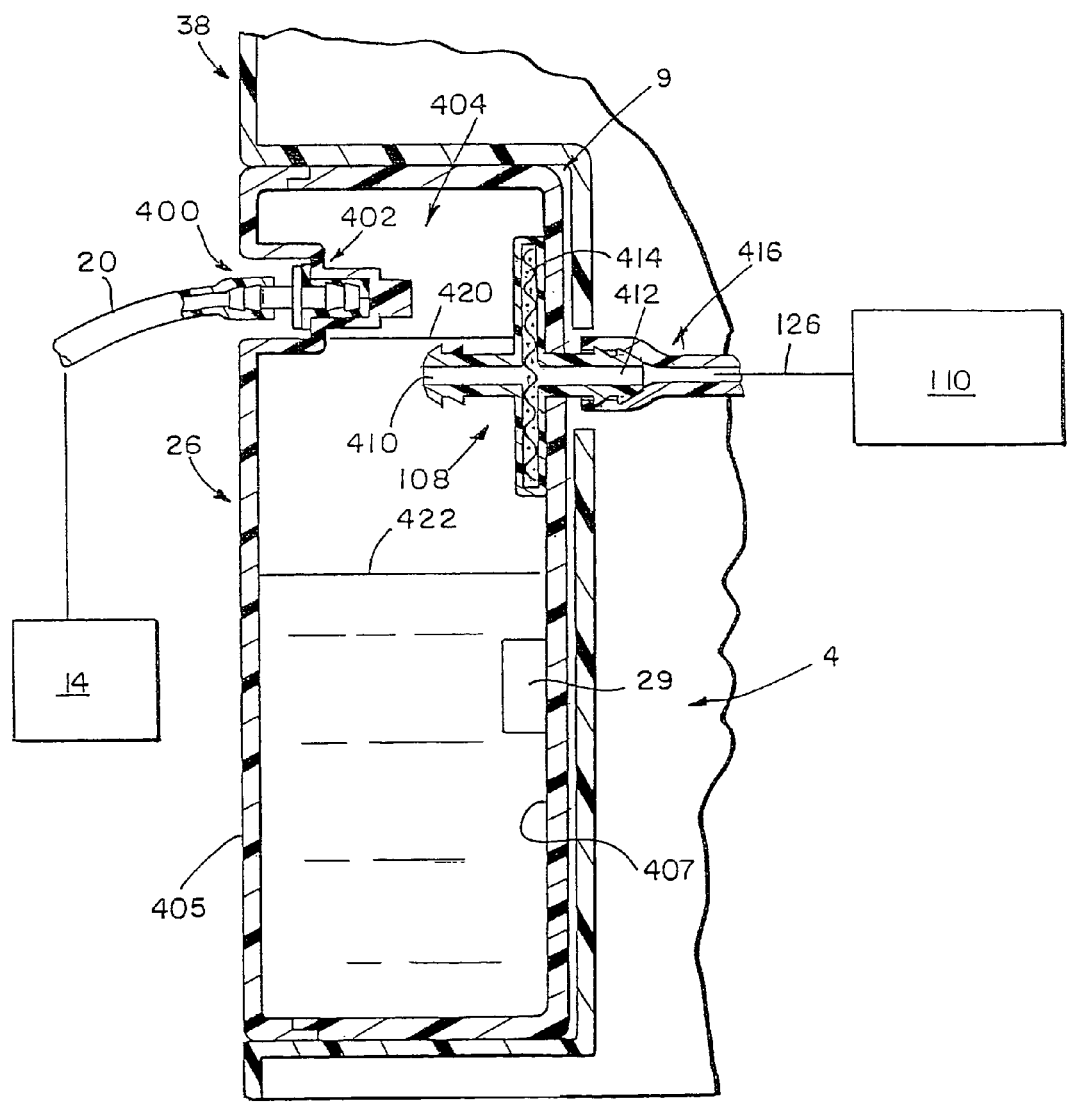

A cross-sectional view of waste canister 26 located in cavity 9 on side 38 of housing 4 is shown in FIG. 6. Tube 20 is connected to a check-valve assembly 400 coupled to recess 402 disposed in the front wall 405 of canister 26. Check valve 400 is configured to allow fluid and exudate from bandage 14 to enter canister 26 and deposit in holding space 404 within canister 26, yet prevent any fluid already in space 404 from exiting through valve 400. Check valve 400, thus prevents fluid from escaping when tube 20 is disengaged from valve 400. In addition, canister 26 can be discarded without any fluid escaping. Hydrophobic filter 108 is located on the rear wall 407 of canister 26. A liquid solidifier 29 is provided in space 404 to decease the fluidity of the exudate. This is a safety measure to lessen the chance of splashing or run-off if canister 26 (or 27) is opened or broken.

Filter 108 in canister 26 is shown having an inlet 410 provided in space 404 and an outlet 412 coupled to a connector 416 with a barrier of hydrophobic material 414 provided there between. As previously discussed, the hydrophobic material allows the vacuum to pass through inlet 410 and outlet 412, yet prevents any fluid from passing. Similar to check valve 400, hydrophobic filter 108 too prevents any fluid from escaping even when canister 26 is removed from housing 4. Outlet 412 of filter 108 is in communication with connector 416. Connector 416 is configured to receive and seal outlet 412 when canister is positioned in cavity 9. Connector 416 is in communication with line 126 and ultimately with pump 110.

In the illustrated embodiment, hydrophobic filter 108 serves as both the canister full mechanism 114 that shuts off the vacuum supply to the canister 26 when the fluid level exceeds the "full" level as indicated by reference numeral 420. When the fluid level is below inlet 410, as indicated by reference numeral 422, fluid continues to enter space 404 through valve 400. When the fluid level 420 is above inlet 410, the fluid is acting as an air block. Fluid cannot pass through filter 108, but because the fluid level is above inlet 410, air cannot pass through either. This causes a dramatic pressure drop (vacuum increase) through line 126. Vacuum pressure transducer 124 is coupled to line 126 measuring the negative pressure passing through canister 26, as previously discussed. If such a dramatic pressure drop occurs, transducer 124 will provide such data to controller 50 through line 128. Controller 50 will then know to shut the system down until the full canister is replaced with either an empty or only a partially full canister.

Figure 8:
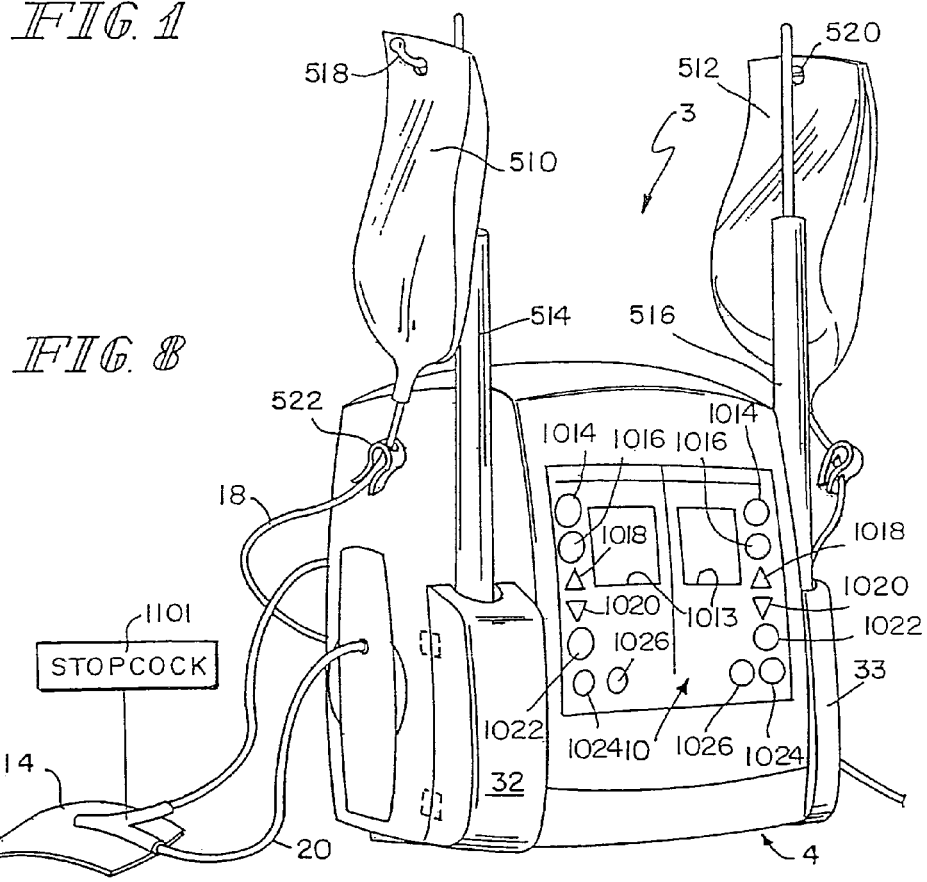

Another illustrative embodiment of a wound treatment apparatus is shown in FIG. 8 and is indicated by reference numeral 3. Apparatus 3 operates in a similar manner as apparatus 2, with the exception of the use of two "intravenous-style" fluid bags 510, 512 suspended above housing 4 to dispense the fluid. In this illustrated embodiment, posts 514, 516 with hooks 518, 520 extend upwardly of apparatus 3 from behind doors 32, 33. It will be appreciated that the posts 514, 516 may be extensible to elevate the bags 510, 512 to selected heights to provide selected pressures for irrigation. A dispensing tube 18 extends from each bag 510, 512 at one end and couples to each bandage. Gravity assists in moving fluid through tubes 18 and into the bandages. A tube clip 522 is coupled to each tube 18 and configured to pinch and close tube allowing the caregiver to selectively prevent fluid from dispensing into bandages.

Illustrative vacuum bandage 314 of FIG. 3 is designed to provide a protective environment around wound 300. Illustratively, such bandages last for up to 7 days without having to be replaced. Bandage 314 includes rinse and drain orifices (not shown) within the body of bandage 314 that communicate with tubes 18, 20, respectively. Such orifices are illustratively 0.030-inch (0.08 cm) diameter and/or 0.040-inch (0.10 cm) diameter. Vacuum evacuating sub-system 66 cooperates with bandage 314, similar to bandage 14, to draw the fluid and exudate from the surface of wound 300, and collect same into waste canister 26.

Examples of bandages 14 and 15 are shown in U.S. patent application Ser. No. 09/725,352, entitled VACUUM THERAPY AND CLEANSING DRESSING FOR WOUNDS, filed on Nov. 29, 2000, and assigned to the same Assignee or Affiliated Assignee as the present disclosure, and the complete disclosure of which is hereby expressly incorporated by reference. It is further contemplated that other bandages may be used with this control system, including bandages having separate irrigation and vacuum ports. Examples of such bandages are shown in U.S. patent application Ser. No. 09/369,113, entitled WOUND TREATMENT APPARATUS, filed on Aug. 5, 1999, and assigned to the same Assignee or Affiliated Assignee as the present disclosure, and the complete disclosure of which is hereby expressly incorporated by reference. The complete disclosure of U.S. patent application Ser. No. 10/144,504, entitled VACUUM THERAPY AND CLEANSING DRESSING FOR WOUNDS and filed on May 13, 2002, is hereby expressly incorporated by reference.

Figure 9:
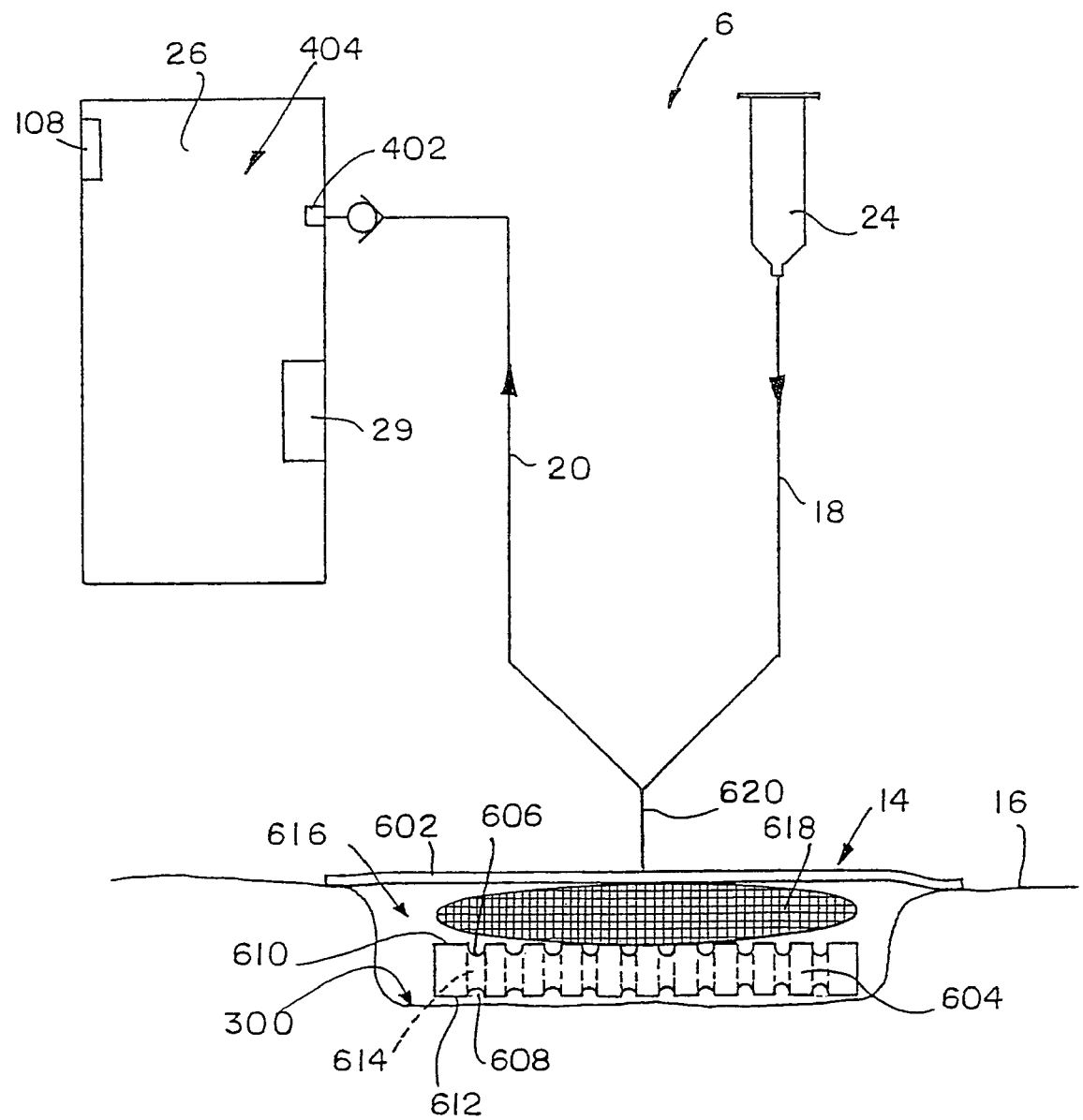

A side diagrammatic view of bandage 14 along with a portion of system 6 is shown in FIG. 9. (See also FIG. 1.) Bandage 14 is of an illustrative type for use with apparatus 2. (Note that the bandage is not drawn to scale.) As previously discussed, bandage 14 is a vacuum bandage. Bandage 14 comprises a cover film 602, illustratively a flexible cover, that seals wound 300 about its outer perimeter. It is contemplated, however, that film 602 can be made from an occlusive or semi-occlusive material that allows water vapor to permeate there through, but otherwise protects wound 300 from the outside environment. A bandage member 604 is placed adjacent wound 300 and is configured to irrigate wound 300. In the illustrated embodiment, bandage member 604 comprises upper channels 606 and lower channels 608, each provided on opposite sides 610, 612, respectively, of bandage member 604. Each of the upper channels 606 is generally congruent with one of the lower channels 608. Channels 606 and 608 are in communication with each other via apertures 614. As shown in the illustrated embodiment, side 612 of bandage member 604 faces wound 300, and side 610 faces a porous packing 618. Packing 618 provided under film 602 to assist in providing a space 616 to facilitate the negative pressure. Packing 618 is typically a gauze material. It will be appreciated, however, that, for some wound care applications, the packing 618 will not be used with member 604 under the film 602.

Illustratively, the caregiver may activate system 6, by means previously described, to draw exudate from wound 300 through channels 606, 608 and apertures 614 of bandage member 604, packing 618 and film 602, through splitter tube 620 connected to evacuating tube 20, and deposit in canister 26. The negative pressure applied to wound 300 created by pump 110 can be applied for a period of time as determined by the caregiver. After a period of drawing, the caregiver may deactivate the negative pressure. The caregiver may begin irrigating wound 300 by releasing fluid from syringe 24, through tube 18, into splitter tube 620, through film 602 and packing 618, and into bandage member 604. The fluid will travel through channels 606 deposit in apertures 614 and irrigate wound 300 by traveling through channels 608. Illustratively, the fluid will continue to irrigate wound 300 until space 616 can no longer receive any more fluid. The fluid is held in space 616 for a period of time as determined by the caregiver. After that period, pump 110 is reactivated and the fluid and exudate from wound 300 is evacuated from bandage 14 and into canister 26 by the manner previously described. This process is repeated as many times as necessary as determined by the caregiver.

In one embodiment, user interface 10 comprises a momentary switch (not shown) that selectively operates the aforementioned process. For example, the switch may be configured such that when the caregiver depresses and holds the switch, the fluid will dispense from syringe 24 into bandage 14. When the caregiver releases the switch the fluid will stop dispensing and pump 110 will activate and begin drawing the fluid and exudate. It is contemplated that the switch may be configured to delay between the vacuuming and dispensing for a period of time that is definable by the caregiver. It is also contemplated that all of the aforementioned descriptions as applied to system 6 are applicable to system 8.

The apparatus 2 is a portable, easy to use topical system that is intended to provide a protective/occlusive environment with features to facilitate the administering of standard wound care. The apparatus 2 provides for the care of two independently controlled wounds. The apparatus 2 provides negative pressure to the wound bed, and the caregiver can set the level of negative pressure. Illustratively, the negative pressure is variable from 25-mmHg to 175-mmHg at increments of 10-mmHg. The caregiver can choose between continuous, intermittent (profile), and no negative pressure modes. It will be appreciated that the apparatus 2 may be set up to provide various levels of vacuum at various times. The apparatus may be provided with the ability to pause negative pressure therapy for set durations of time. The system may be set up to provide audible alarms to remind the caregiver to reset or start a new cycle of vacuum therapy.

The apparatus 2 is intended to provide an occlusive wound healing environment. The apparatus 2 provides an active therapy unit that delivers drainage and cleansing for aggressive wound healing. It is intended, for example, for use on all pressure ulcers (Stage II through Stage IV), surgical draining wounds and leg ulcers.

Figure 7:
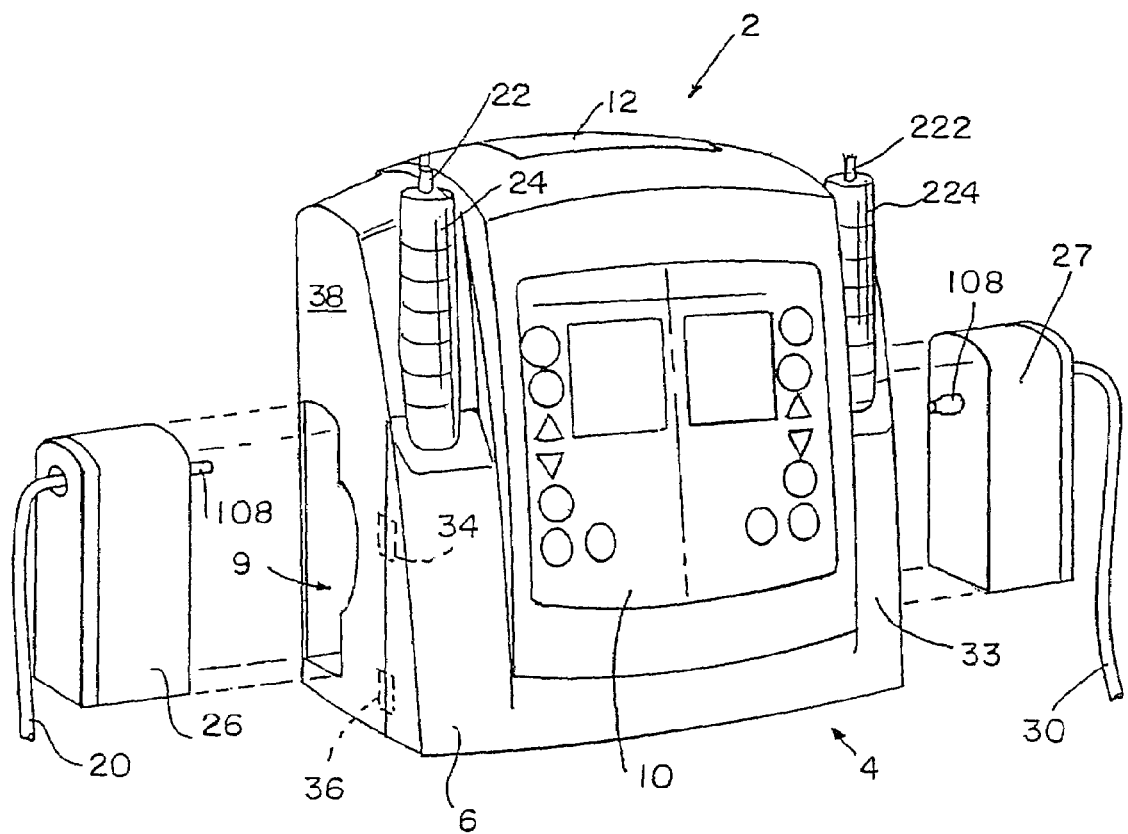
Figure 10:
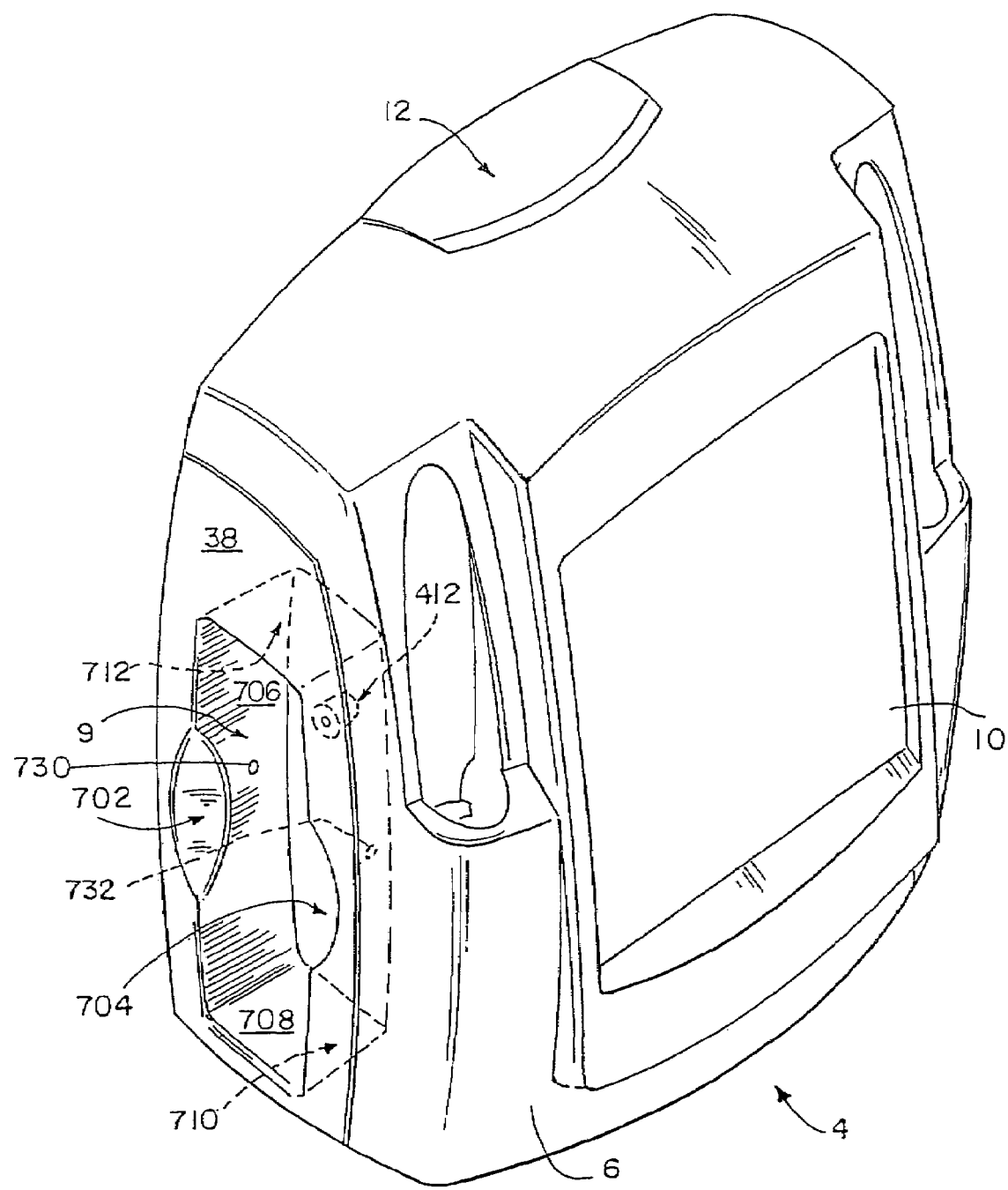
Figure 11:
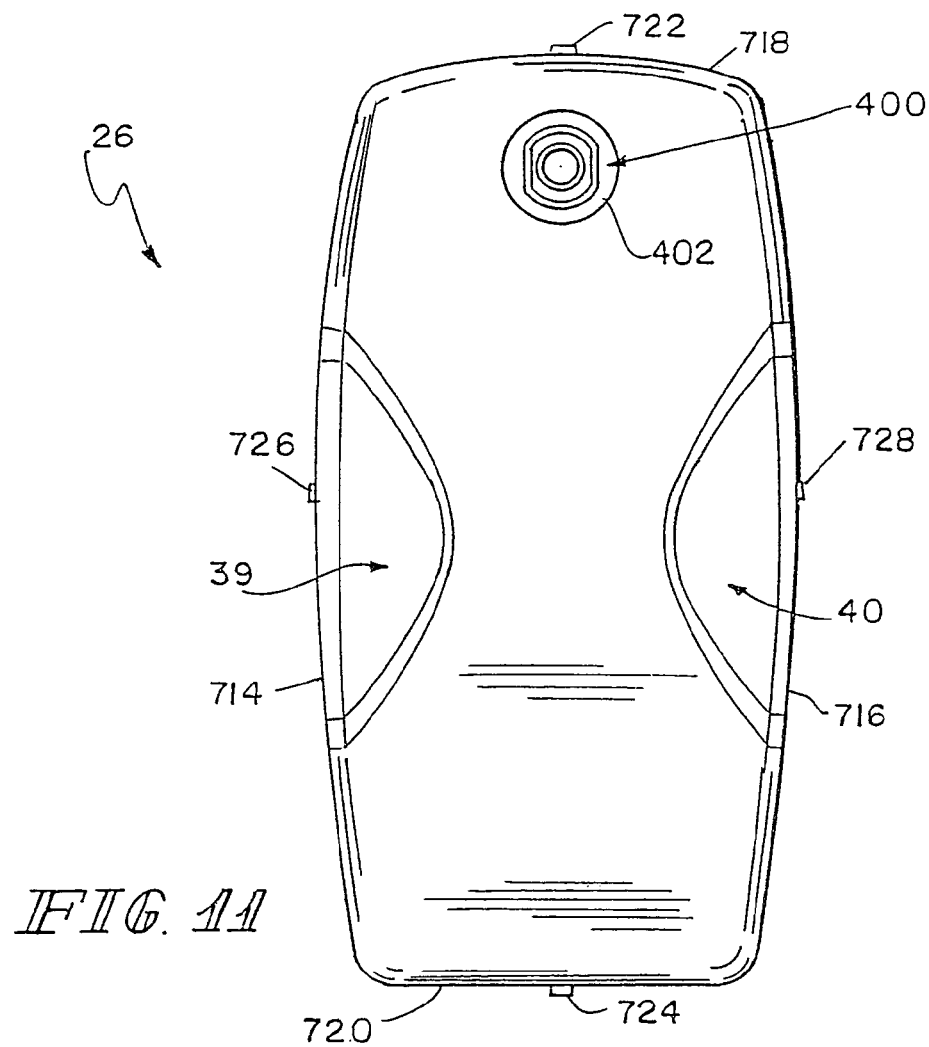
Figure 13:
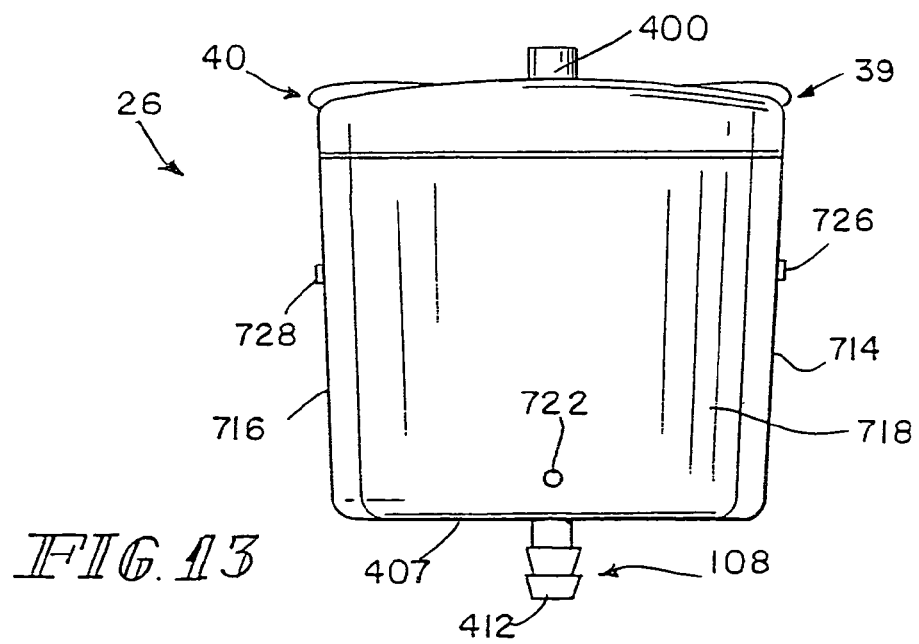
Figure 12:
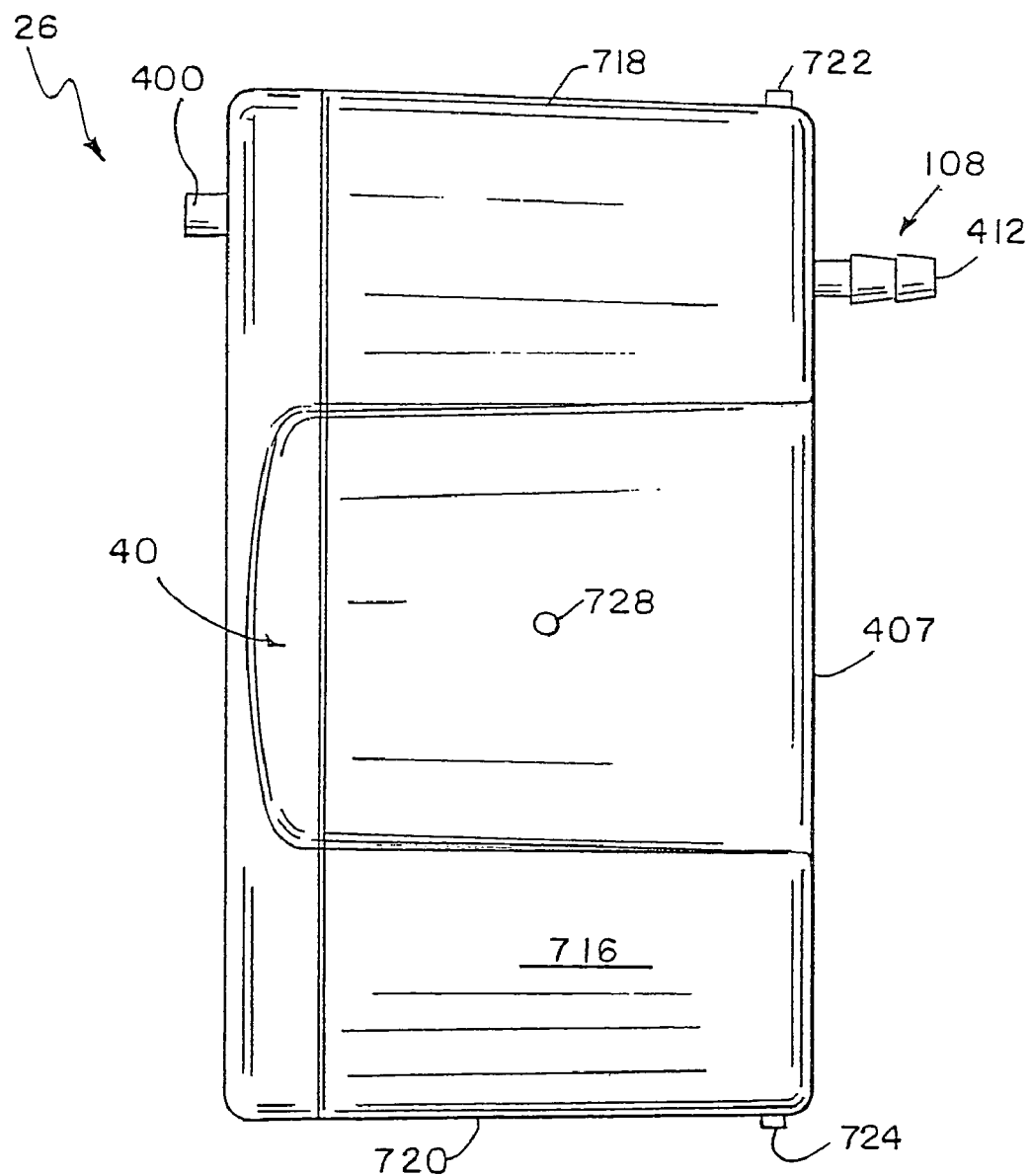

In the illustrated embodiment, as shown in FIGS. 7 and 10, for example, canister 26 is configured to be received in cavity 9 disposed in side 38 of housing 4. As shown specifically in FIG. 10, cavity 9 comprises two pull recesses 702, 704. Such recesses 702, 704 are concave-shaped portions formed adjacent to side 38 and to side walls 706 and 708. Recesses 702, 704 are provided to allow finger clearance when the caregiver grasps grip portions 39, 40 of canister 26 to remove it from, or insert it into cavity 9. (See also FIGS. 1, 11 and 13.) Side walls 706, 710 and bottom and top walls 708, 712 define cavity 9 such that cavity 9 provides a relatively conforming receptacle for the canister 26. The walls 706, 710 and 708, 712 conform to the size and shape of the panels 714, 716, 718, 720 of canister 26. (See FIGS. 12 and 13.) Outlet 412 of filter 108 mates with connector 416 to produce an air-tight seal between port 412 and connector 416. It is further contemplated that other structures or configurations of outlet 412 and connector 416 can be used to ensure system 6 is a closed system when canister 26 is properly coupled to housing 4. It is still further contemplated that the aforementioned descriptions of canister 26 of system 6 apply equally to canister 27 of system 8.

Each of top and bottom panel 718, 720 of canister 26 includes a boss 722, 724, respectively. Each boss 722, 724 is configured to engage a sensor such as sensor 116, 118, respectively, as depicted in FIG. 2. This engagement provides a signal to controller 50 indicating that canister 26 is seated properly into cavity 9 and the vacuum therapy treatment may begin to be administered. It is contemplated that bosses 722, 724 can be mechanical sensors, optical, capacitive or other similar type sensors.

Side panels 714, 716 include buttons 726, 728 to assist the caregiver in placing canister 26 in the proper location within cavity 9. Illustratively, buttons 726, 728 are small protrusions, each extending from a side panel. Each button 726, 728 is configured to be received or "snapped" into corresponding dimples 730, 732, respectively, disposed in walls 706, 710, respectively. In the illustrated embodiment, the buttons extend from the widest point of side panels 714, 716 of canister 26.

Figure 14:
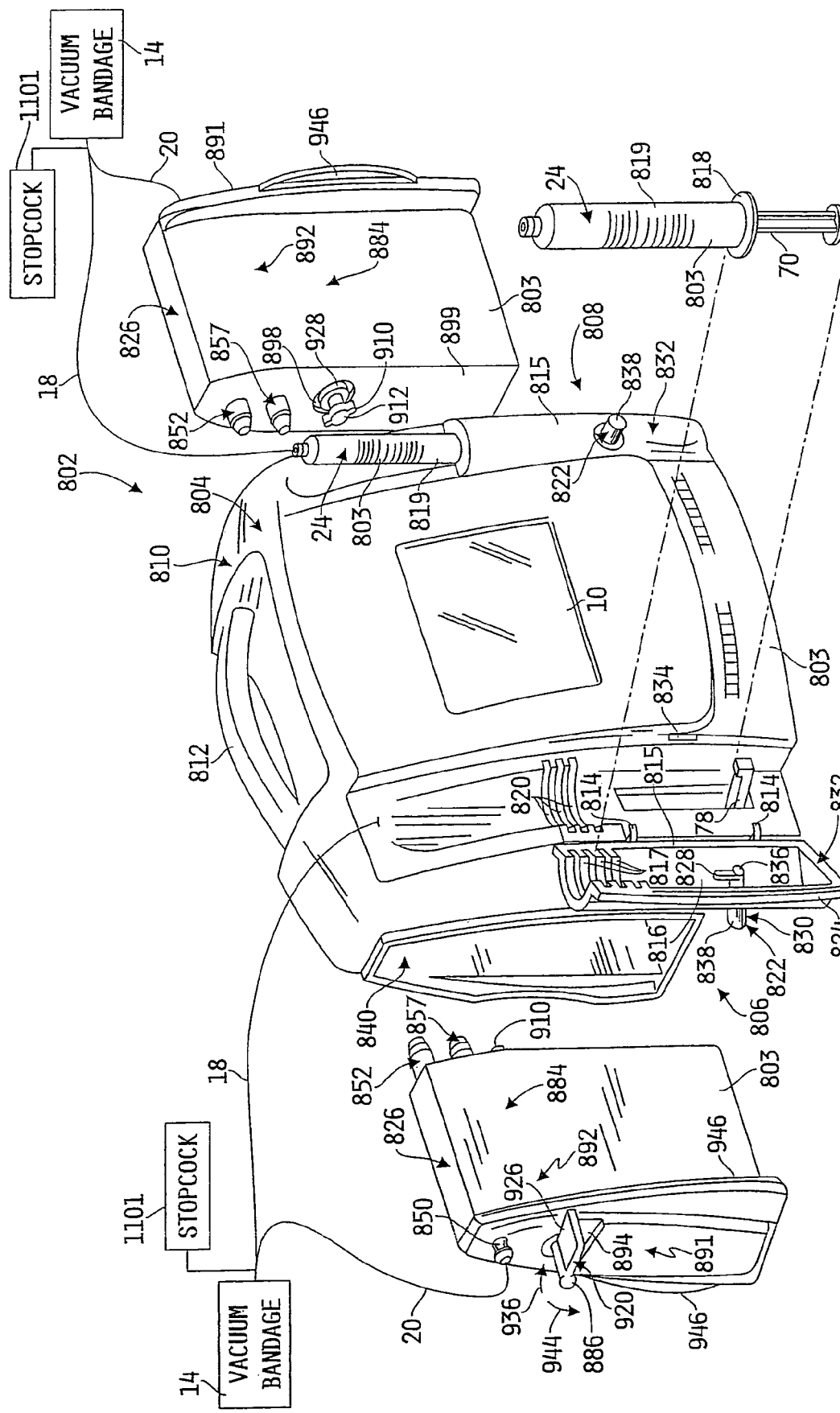

Another wound treatment apparatus 802 is illustrated in FIG. 14. Apparatus 802 is similar in structure and function to apparatus 2, except as otherwise noted, so that identical reference numbers refer to similar components. Apparatus 802 has a pair of vacuum wound bandages 14, a pair of dispensing lines 18, a pair of evacuating lines 20, and a main control unit 803 adapted for use with bandages 14 and lines 18, 20. Bandages 14, lines 18, 20, and control unit 803 cooperate to provide dual vacuum therapy systems 806, 808.

Control unit 803 has a control module 810, a pair of fluid sources such as syringes 24 coupled to dispensing lines 18 to provide fluid for irrigation of the wounds, and a pair of disposable waste collection canisters 826 coupled to evacuating lines 20 to collect waste material such as exudate from the wounds and fluid from syringes 24, as illustrated in FIG. 14. Each dispensing line 18 and evacuating line 20 is associated with one of bandages 14. Each syringe 24 and canister 826 is provided for one of systems 806, 808. Control module 810 has a housing 804. Syringes 24 are coupled to the front of housing 804 and canisters 826 are coupled to the sides of housing 804, as discussed in more detail below. Housing 804 has a handle 812 at the top thereof for hand-carrying control unit 803. A user interface 10 is centrally mounted to housing 804 between syringes 24 and canisters 826 to allow a caregiver to operate systems 806, 808.

Systems 806, 808 are similar to one another in structure and function. Thus, the following description of system 806 applies also to system 808.

Figure 17:
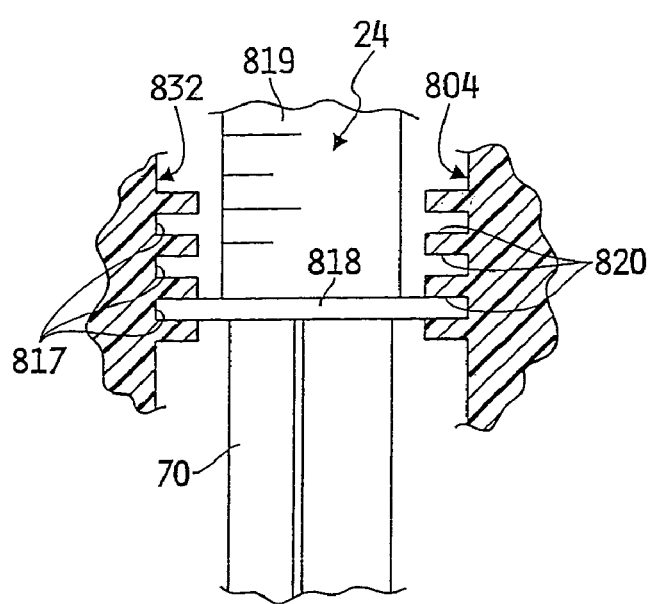

Housing 804 has a door 832 to partially cover syringe 24, as illustrated in FIG. 14. Door 832 is hinged to housing 804 by a pair of vertically-spaced hinges 814 positioned along a laterally outer side 815 of door 832 for movement of door 832 between opened and closed positions. A rear side 816 of door 832 has a plurality of vertically-spaced, horizontal mounts or grooves 817 (see FIGS. 14 and 17) for receiving a flange 818 of syringe 24. Housing 804 also has a plurality of corresponding vertically-spaced, horizontal mounts or grooves 820 (see FIGS. 14 and 17) for receiving flange 818. During installation of syringe 24, an end of a plunger 70 of syringe 24 is placed on a vertically movable plunger interface 78 of a syringe drive mechanism, such as the one described above in connection with apparatus 2, and flange 818 is inserted into one of grooves 820. Door 832 is then closed causing one of grooves 817 to receive flange 818 so that syringe 24 is held in place by grooves 817, 820. Grooves 817, 820 support syringe 24 in a vertical orientation.

Figure 15:
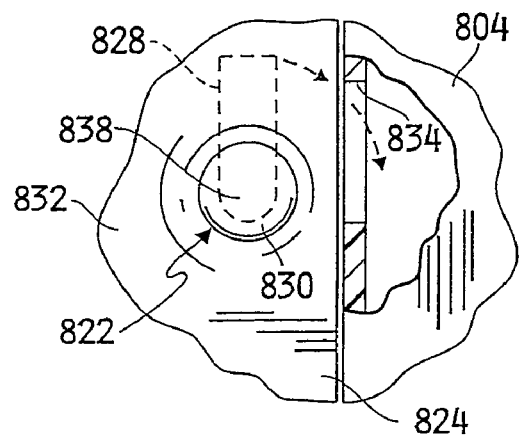
Figure 16:
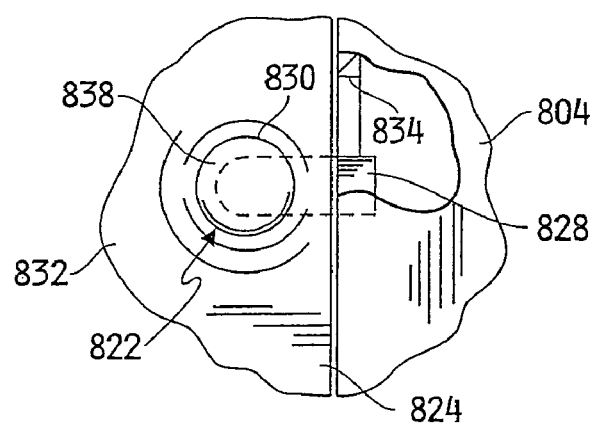

A door latch 822 is coupled to a laterally inner side 824 of door 832, as illustrated in FIGS. 14-16. Latch 822 is movable relative to door 832 between a latched position (FIG. 16) blocking movement of door 832 from its closed position to its opened position and a release position (FIGS. 14-15) allowing door 832 to move between its closed position and its opened position. Latch 822 has a fastener 828, such as an arm or lug, and an actuator 830 to pivot fastener 828 into and out of a slot 834 of housing 804 between the latched and release positions. Actuator 830 has a stem 836 coupled to fastener 828 and a handle or door knob 838 coupled to stem 836 to rotate stem 836 and thus fastener 828 between the latched and release positions when a caregiver rotates handle 838. Stem 836 extends through an aperture of door 832. Handle 838 is coupled to one end of stem 836 in front of door 832 and fastener 828 is coupled to an opposite end of stem 836 behind door 832.

Figure 27:
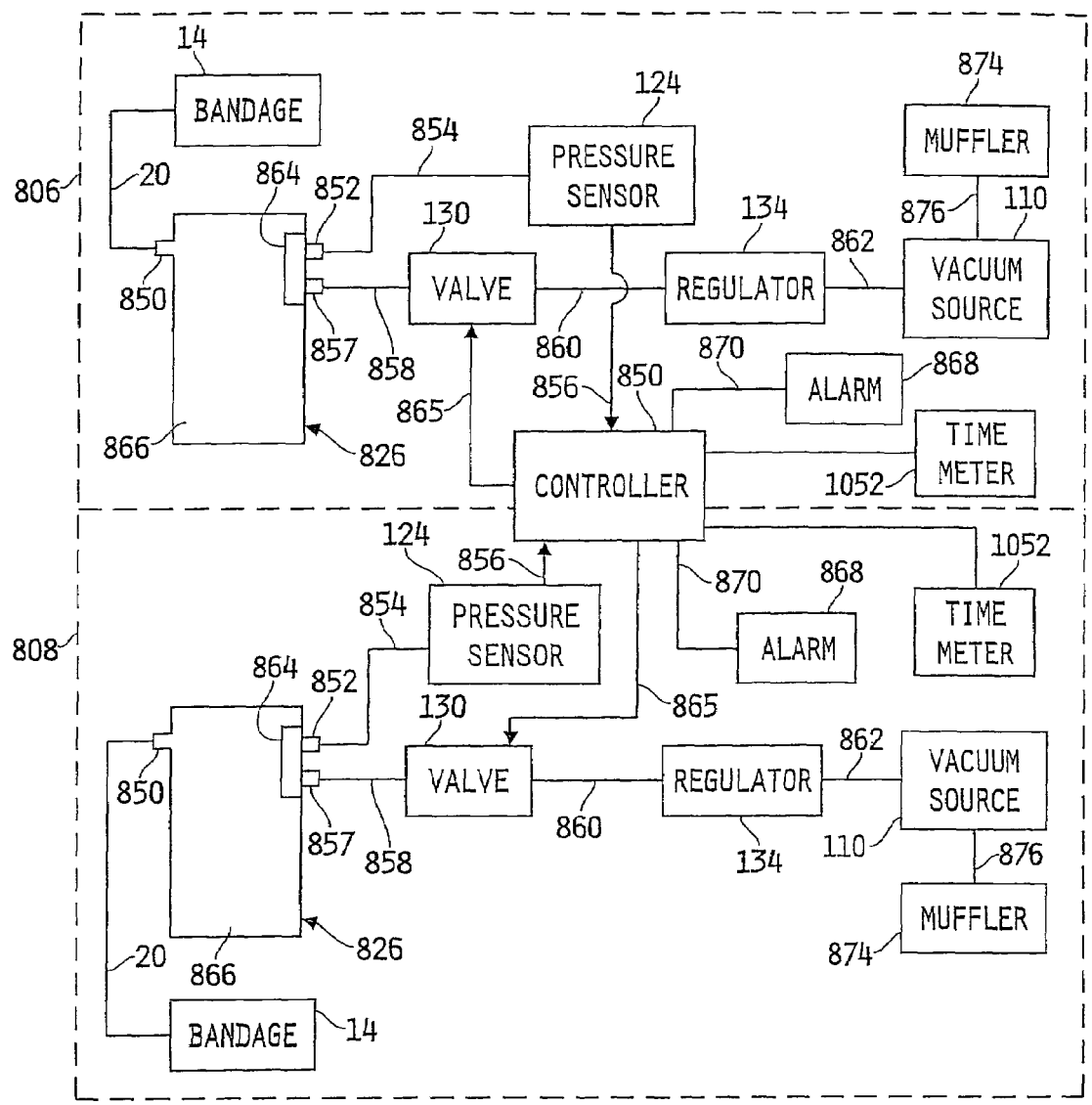
FIG. 27 is a diagrammatic view of portions of the wound treatment apparatus of FIG. 14.

Canister 826 is coupled to vacuum bandage 14 and other components of apparatus 802, as illustrated, for example, in FIG. 27. Evacuating line 20 is coupled to vacuum bandage 14 and an inlet port 850 of canister 826 to introduce waste material into an interior region or chamber 866 of canister 826 through inlet port 850. A pressure sensor 124 is coupled to an upper pressure port 852 of canister 826 via a fluid line 854

(see FIGS. 19 and 27) to sense the pressure in region 866. Pressure sensor 124 sends a signal indicative of the sensed pressure to a controller 850, which is common to both systems 806, 808, via an electrical line 856 (see FIG. 27). A proportional valve 130 (see FIGS. 19 and 27) is coupled to a lower outlet port 857 of canister 826 via a fluid line 858 (see FIGS. 19 and 27). A pressure regulator 134 (see FIGS. 19 and 27) is coupled to proportional valve 130 and a vacuum source 110 (see FIGS. 19 and 27) via fluid lines 860 and 862, respectively (see FIG. 27). Vacuum source 110 provides a negative or vacuum pressure within bandage 14 through lines 862, 860, 858, 20 and regulator 134, valve 130, and canister 826 to suction waste material into canister 826.

Vacuum source 110 continues to operate even if, for example, blockage occurs somewhere upstream from vacuum source 110. If the blockage becomes too great, vacuum source 110 could experience too great a load, or vacuum pressure. Pressure regulator 134 is provided to establish a maximum load that vacuum source 110 can experience. Pressure regulator 134 allows air to be suctioned into line 862 when this maximum load is reached to protect vacuum source 110.

Figure 20:
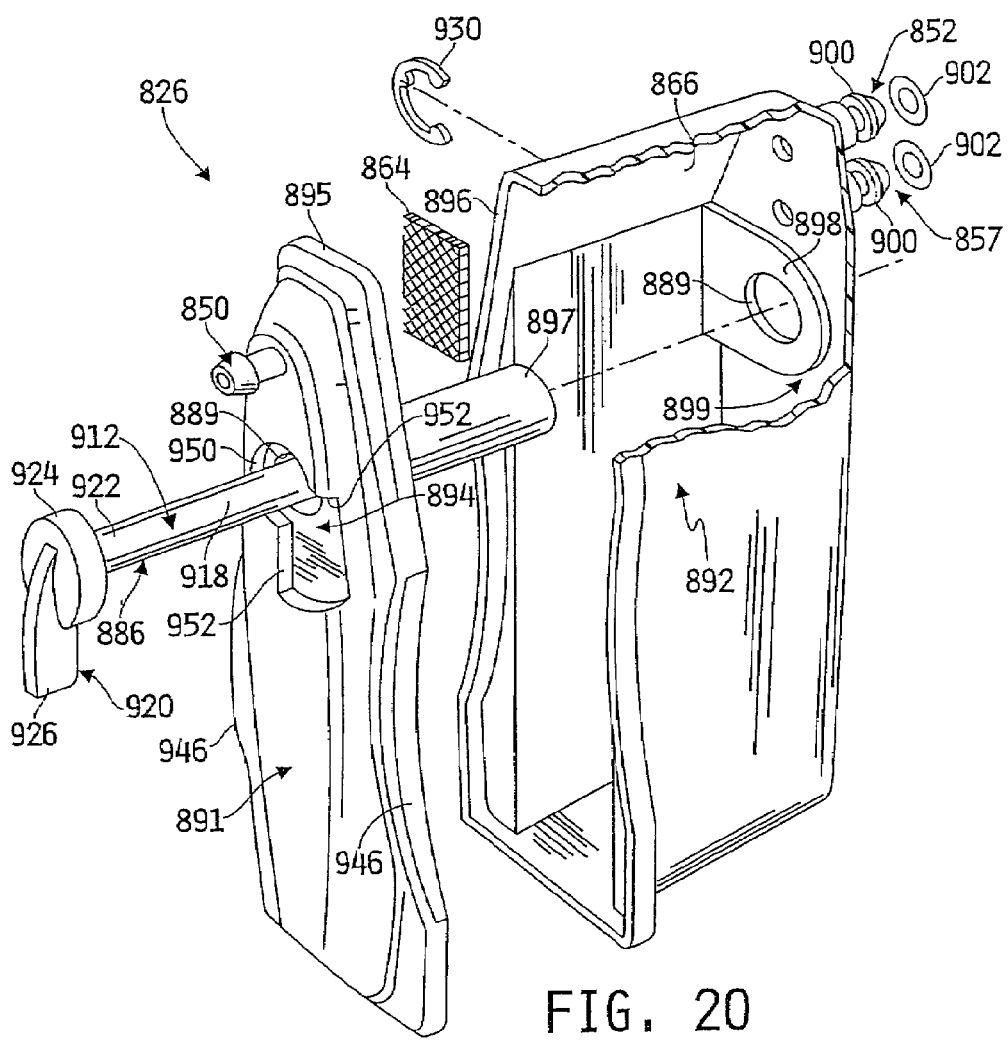
FIG. 20 is an exploded perspective view of a waste collection canister of the control unit.

A filter 864 is positioned in interior region 866, as shown in FIGS. 20, 23, and 27. Filter 864 covers pressure port 852 and outlet port 857 to prevent waste material from entering lines 856, 858 and possibly damaging pressure sensor 124, proportional valve 130, pressure regulator 134, or vacuum source 110. Filter 864 is, for example, a 1.0 micron teflon hydrophobic filter.

Controller 850, pressure sensor 124, and proportional valve 130 cooperate to provide feedback control of the vacuum pressure provided to bandage 14. Controller 850 operates proportional valve 130 via electrical line 864 in response to the pressure sensed by pressure sensor 124 to provide a desired negative pressure in interior region 866. A caregiver provides the desired negative pressure to controller 850 through user interface 10. If, for example, pressure sensor 124 senses a pressure in canister 826 that is more negative than the desired negative pressure (which includes a suitable tolerance range), controller 850 will cause valve 130 to move closer toward its fully closed position so that interior region 866 experiences less of the suction from vacuum source 110 and the pressure in canister 826 rises to approach the desired negative pressure. On the other hand, if pressure sensor 124 sense a pressure in canister 826 that is more positive than the desired negative pressure, controller 850 will cause valve 130 to move closer to its fully opened position so that interior region 866 experiences more of the suction from vacuum source 110 and the pressure in canister 826 lowers to approach the desired negative pressure.

Based on readings from pressure sensor 124, controller 850 is able to detect when the waste material in canister 826 has reached a fill limit, which occurs when the waste material at least partially occludes outlet port 857. As outlet port 857 becomes occluded due to the wetting of filter 864, the negative pressure established by vacuum source 110 becomes blocked from interior region 866. The pressure sensed by sensor 124 then begins to rise (i.e., become less negative) above the desired negative pressure, especially if bandage 14 has a vent in communication with atmosphere, and air enters interior region 866 through bandage 14, line 20, and inlet port 850. In some embodiments, air enters interior region 866 through a bleed port (not shown) formed in housing 884 at an elevation higher than outlet port 857 instead of through the bandage vent or in addition to the bandage vent. In response to the pressure rise, controller 850 moves proportional valve 130 toward its fully opened position to try to lower the sensed pressure to the desired negative pressure. If vacuum source 110 is able to lower the sensed pressure to the desired negative pressure, the waste material fill limit has not been reached. If the sensed pressure remains above the desired negative pressure, controller 850 opens proportional valve 130 further and compares the sensed pressure to the desired negative pressure.

Controller 850 determines that the waste material in canister 826 has reached its fill limit when proportional valve 130 has been fully opened but the sensed pressure remains above the desired negative pressure. This occurs because the waste material has occluded outlet port 857 enough to prevent vacuum source 110 from being able to lower the sensed pressure to the desired negative pressure. Pressure sensor 124, however, is still able to sense the pressure within interior region 866 through pressure port 852 because pressure port 852 is positioned at an elevation higher than outlet port 857. Controller 850 then activates an alarm 868 via an electrical line 870 to alert a caregiver that canister 826 is full and needs to be changed.

Figure 18:
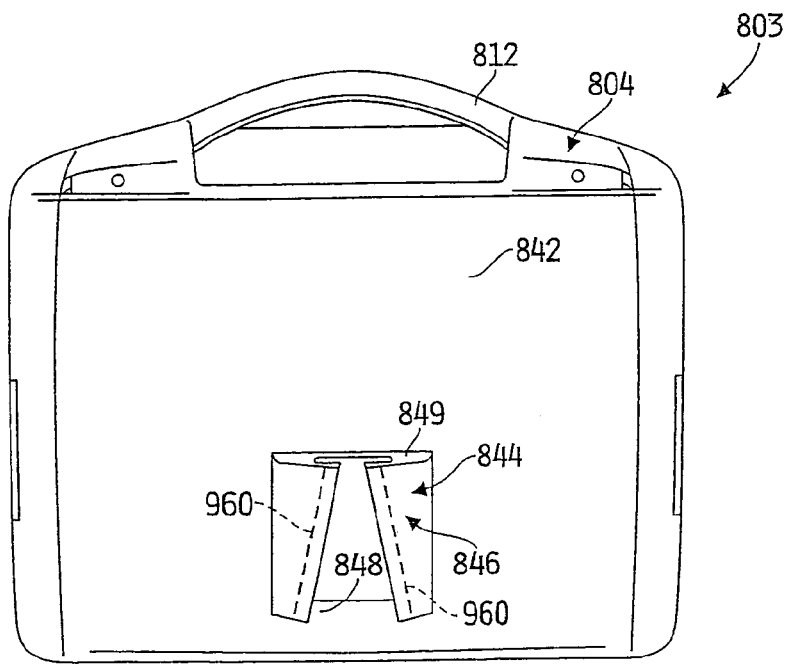
FIG. 18 is a perspective view of the rear of a control unit of the wound treatment apparatus of FIG. 14 showing a carrying handle at the top of the control unit and a mounting bracket on a rear wall of the control unit.
Figure 19:
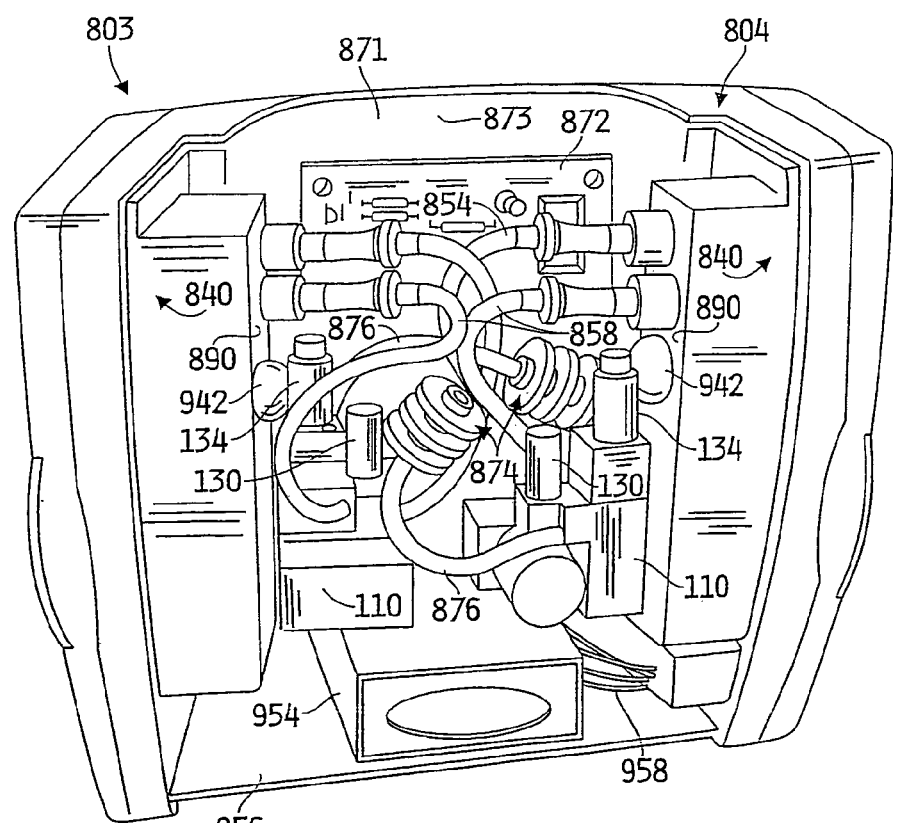
FIG. 19 is a perspective view of the rear of the control unit of FIG. 18 with a rear wall removed.

Housing 804 contains components of control unit 803, as illustrated in FIG. 19. Housing 804 has two receptacles 840, one receptacle 840 on each side of housing 804; and each receptacle 840 is configured to receive a respective canister 826 therein. Housing 804 also has a removable vertical rear wall 842 (see FIG. 18). Behind rear wall 842 is a chamber 871 (see FIG. 19). Each receptacle 840 extends toward a center of chamber 871 from a side wall of housing 804. A printed circuit board (PCB) 872 is mounted to a rear surface of a front wall 873 of housing 804 within chamber 871. Pressure sensors 124 and controller 850 are mounted to PCB 872 within chamber 871. Valves 130, pressure regulators 134, vacuum sources 110, and lines 854, 858 are also positioned within chamber 871.

A pair of mufflers 874 and a pair of muffler lines 876 are positioned within chamber 871. Each muffler line 876 is coupled to one of mufflers 874 and one of vacuum sources 110. Illustratively, each muffler 874 has three disk filters 878 in series to provide three chambers 880 having glass fiber material 882 therein to absorb sound energy. Adjacent filters 878 are coupled together by luer-lock mechanisms.

A battery 954 rests on a bottom wall 956 of housing 804 in chamber 871, as illustrated in FIG. 19. A main power connection 958 is coupled to battery 954 and to PCB 872. Battery 954 is illustratively a rechargeable nickel metal hydride battery that automatically recharges when main power connection 958 is coupled to an external electrical outlet (not shown) via a power cord (not shown), for example, and automatically provides electrical power to the electrical components of control unit 803 when battery 954 is charged and the power cord is disconnected from the external electrical outlet.

A mounting bracket 844 is coupled to an outwardly facing surface of rear wall 842, as illustrated in FIG. 18, to mount control unit 803 to a suitable control unit support (not shown). Bracket 844 has an envelope 846 to receive the support through a lower opening 848. A horizontal upper wall 849 is coupled to the top of envelope 846. Envelope 846 has internal tapered walls 960 extending from the bottom of envelope 846 to upper wall 849. The control unit support wedges against tapered walls 960 when it is inserted within envelope 846.

Canister 826 has a housing 884 providing interior region 866 to collect waste material therein and a latch 886 to couple housing 884 to housing 804 of control module 810, as illustrated in FIGS. 14 and 20-23. Canister 826 further has a cylindrical sleeve 888 carried by housing 884 and extending horizontally through interior region 866. Ends of sleeve 888 are appended to respective outer and inner vertical walls 891, 899 of housing 884. Walls 891, 899 are each formed with an aperture 889 that communicates with an interior region of sleeve 888. Latch 886 extends through apertures 889 and sleeve 888 and engages a vertical back wall 890 of receptacle 840, as described in more detail below.

Outer vertical wall 891 of housing 884 and sleeve 888 cooperate to provide a monolithic unit that is coupled, such as by RF or ultrasonic welding or adhesive, to a main portion 892 of housing 884 (see FIGS. 20-23). An outer end portion 893 of sleeve 888 is formed monolithically with a recessed portion 894 of wall 891. Wall 891 has a peripheral flange 895 that is coupled to a corresponding peripheral flange 896 of main portion 892. An inner end portion 897 of sleeve 888 is coupled to a recessed portion 898 of inner vertical wall 899 of main portion 892. Outer wall 891 has inlet port 850 formed integrally therewith or appended thereto. Inner wall 899 has upper pressure port 852 and lower outlet port 857 formed integrally therewith or appended thereto.

Figure 21:
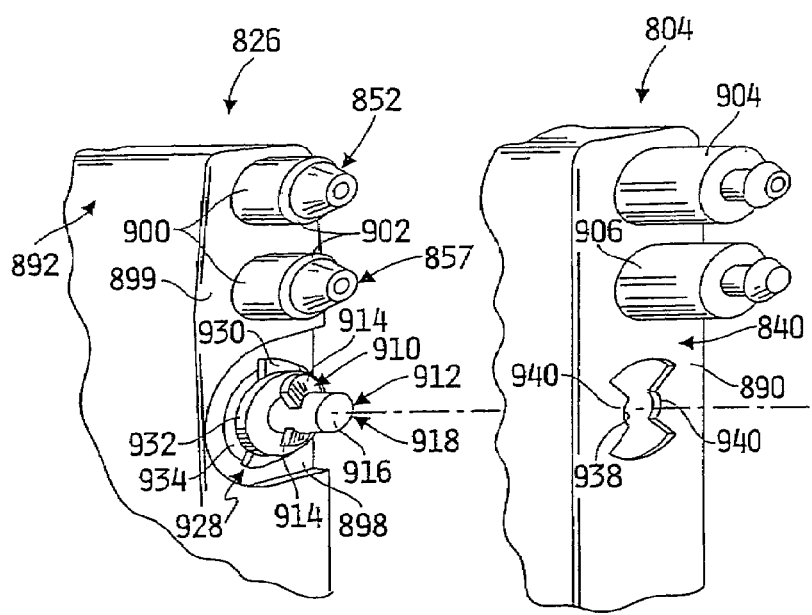
FIG. 21 is a fragmentary perspective view of a portion of the canister of FIG. 20 and a portion of a receptacle of the housing in which the canister is received.
Figure 22:
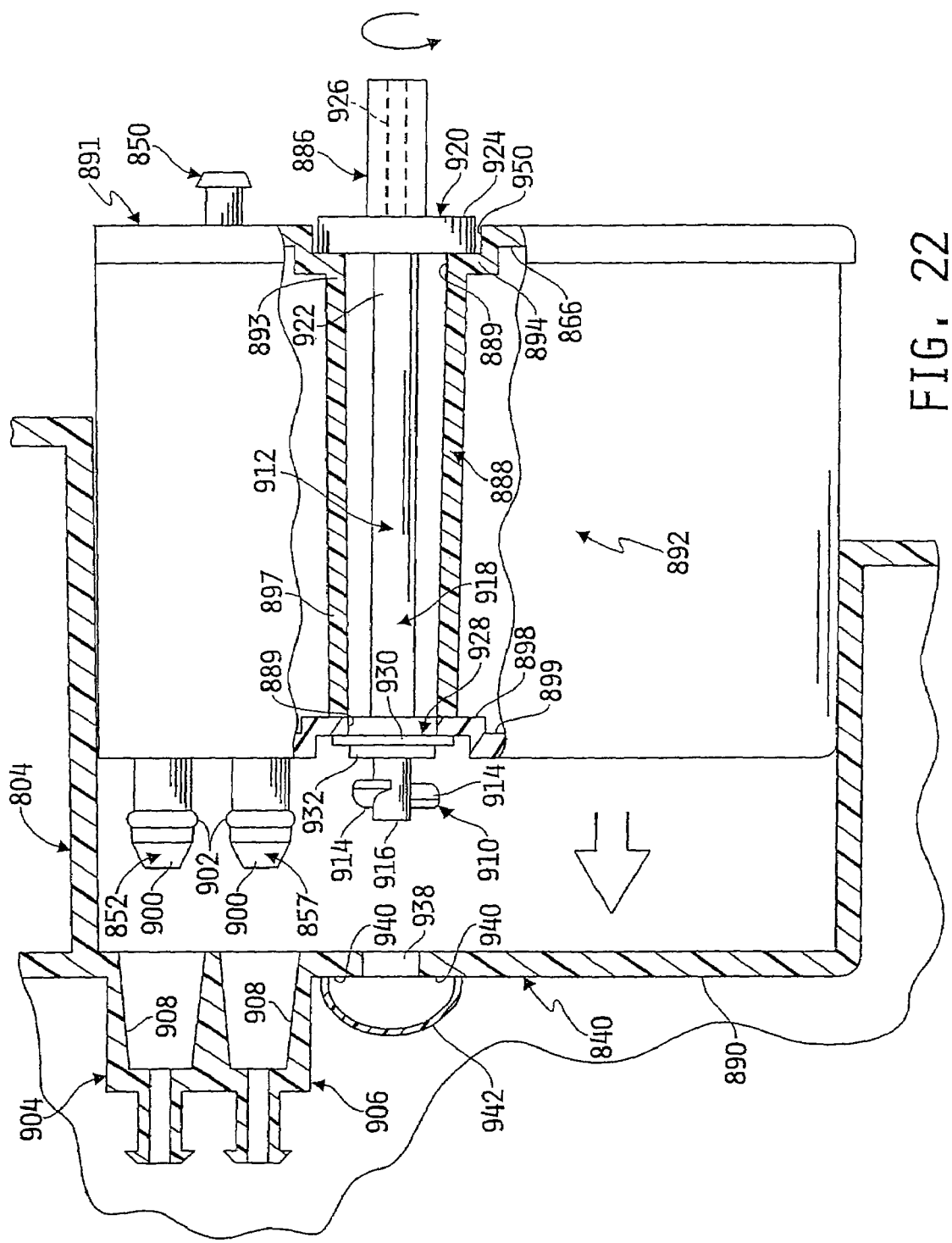
FIG. 22 is a side sectional view of the canister partially inserted into the receptacle.

Latch 886 has a fastener 910 to couple to back wall 890 and an actuator 912 to rotate fastener 910, as illustrated in FIGS. 21-23. Fastener 910 has a pair of bayonet-style canted lugs 914 coupled to an inner end portion 916 of a shaft 918 of actuator 912. Lugs 914 are diametrically opposed to one another and extend somewhat circumferentially and axially on shaft 918.

Actuator 912 further has a handle 920 coupled to an outer end portion 922 of shaft 918, as illustrated in FIGS. 14, 20, 22 and 23. Handle has a disk 924 coupled to end portion 922 and a flange 926 coupled to and extending radially outwardly from disk 924. Disk 924 and a portion of flange 926 are positioned within recessed portion 894. Recessed portion 894 has a pair of stop edges 952 (see FIG. 20) positioned to restrict rotation of flange 926 to about 90 degrees.

A retainer 928 (see FIGS. 21-23) is mounted to shaft 918 between handle 920 and fastener 910. Illustrative retainer 928 has a clip 930, such as an e-clip, and a clip mount 932. Clip mount 932 takes the form of a disk mounted to shaft 918 and has a circumferential groove 934 configured to receive clip 930. Disk 932 has a diameter smaller than the inner diameter of sleeve 888 to facilitate insertion of fastener 910 through sleeve 888 during assembly of canister 826. After insertion of fastener 910 through sleeve 888, clip 930 is positioned in groove 934 to engage recessed portion 898 to prevent latch 886 from inadvertently withdrawing from sleeve 888. An inner portion of disk 932 is received in one of apertures 889 and disk 924 is received in a space defined by an arcuate edge 950 (see FIGS. 20, 22, and 23) of wall 891 to support latch 886 for rotation relative to housing 884.

Figure 26:
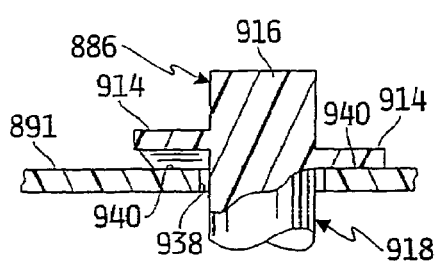
FIG. 26 is a sectional view taken along line 26-26 of FIG. 25 showing engagement between the lugs and the receptacle wall.
Figure 28:
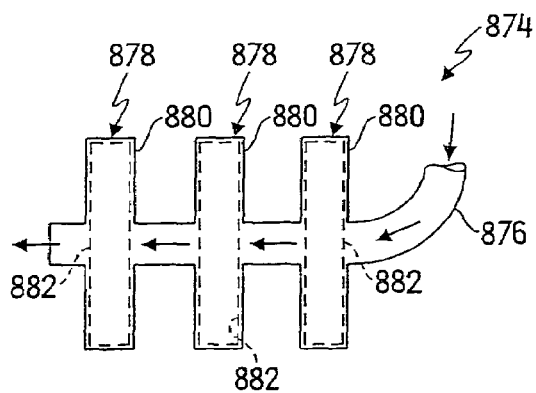
FIG. 28 is a diagrammatic view of a three-chambered muffler.

After latch 886 is coupled to housing 884, canister 826 is ready to be installed within receptacle 840. A caregiver places canister 826 within receptacle 840 (see FIG. 22) and inserts leading edges of lugs 914 through an aperture 938 of back wall 890 shaped to receive lugs 914 (see FIG. 24). The caregiver then rotates handle 920, and thus lugs 914, by hand, for example, approximately 90 degrees in a direction 936 (see FIG. 25). This rotation causes lugs 914 to cam against inwardly facing thrust surfaces 940 of back wall 890 (see FIG. 26) so that canister 826 moves toward back wall 890 and pressure port 852 and outlet port 857 are drawn into corresponding upper 904 and lower 906 sockets, respectively, of back wall 890 (see FIGS. 22-23). Each port 852, 857 has a nipple 900 that is inserted into the respective socket 904, 906 and an O-ring 902 surrounding nipple 900. When lugs 914 are rotated against surfaces 940, nipples 900 are drawn into sockets 904, 906 so that O-rings 902 sealingly engage tapered walls 908 of sockets 904, 906. Sockets 904, 906 provide portions of lines 854, 858, respectively. A dome cover 942 is positioned on an inner surface of back wall 890 and over lugs 914 and inner end portion 916 of shaft 918.

Canister 826 is removed from receptacle 840 and disposed of when canister 826 is fall of waste material. To do so, a caregiver removes line 20 from inlet port 850, places a cap (not shown) on port 850 to prevent spillage, and rotates handle 920 in a reverse direction 944 to release lugs 914 from back wall 890. The caregiver then pulls on side grips 946 (see FIG. 14) of canister 826 to remove canister 826 from receptacle 840. As canister 826 is removed from receptacle 840, lugs 914 pass back through aperture 938 and pressure port 852 and outlet port 857 are withdrawn from upper and lower sockets 904, 906. Canister 826 can then be discarded and a new, empty canister 826 can be installed within receptacle 840.

By having latch 886 included as part of canister 826, which is disposed of after being filled with waste material, latch 886 is not used over and over again, thereby preventing lugs 914 from wearing down and degrading the sealed connection between ports 852, 857 and sockets 904, 906.

Although the foregoing apparatus has been described, one skilled in the art can easily ascertain the essential characteristics of the apparatus, and various changes and modifications may be made to adapt the various uses and characteristics without departing from the spirit and scope of this disclosure, as described by the claims which follow.

What is claimed is:

1. A canister adapted for use with a vacuum wound bandage associated with a wound of a patient and a control module to provide a negative pressure through the vacuum wound bandage to treat the wound, the canister comprising
a housing having an interior region to collect waste material from the vacuum wound bandage,
a latch coupled to the housing and operable to couple the housing to the control module, the latch extending through the interior region of the housing, and
a sleeve carried by the housing and positioned within the interior region, wherein a portion of the latch is positioned within the sleeve,
wherein the housing has a first vertical wall and a second vertical wall, and the sleeve extends from the first vertical wall to the second vertical wall, and
wherein the first vertical wall has a first recessed portion, the second vertical wall has a second recessed portion, and the sleeve has a first end portion coupled to the first recessed portion and a second end portion coupled to the second recessed portion.

2. A canister adapted for use with a vacuum wound bandage associated with a wound of a patient and a control module to provide a negative pressure through the vacuum wound bandage to treat the wound, the canister comprising
a housing having an interior region to collect waste material from the vacuum wound bandage,
a latch coupled to the housing and operable to couple the housing to the control module, the latch extending through the interior region of the housing, and
a sleeve carried by the housing and positioned within the interior region, wherein a portion of the latch is positioned within the sleeve,
wherein the housing has a first vertical wall and a second vertical wall, and the sleeve extends from the first vertical wall to the second vertical wall,
wherein the first vertical wall has a first recessed portion, the second vertical wall has a second recessed portion, and the sleeve has a first end portion coupled to the first recessed portion, and wherein the latch has a handle positioned for rotation within the first recessed portion and a retainer to engage the second recessed portion to maintain the latch within the sleeve.

3. A canister adapted for use with a vacuum wound bandage associated with a wound of a patient and a control module to provide a negative pressure through the vacuum wound bandage to treat the wound, the canister comprising
 a housing having an interior region to collect waste material from the vacuum wound bandage,
 a latch to couple the housing to the control module, the latch extending through the interior region, and
 a sleeve carried by the housing and positioned within the interior region, wherein a portion of the latch is positioned within the sleeve, and
 wherein the housing has a first vertical wall and a second vertical wall, the first vertical wall has a first recessed portion, the second vertical wall has a second recessed portion, and the sleeve has a first end portion coupled to the first recessed portion and a second end portion coupled to the second recessed portion, the latch has a handle positioned for rotation within the first recessed portion and the first recessed portion is configured to limit rotation of the handle to about 90 degrees.

4. A canister adapted for use with a vacuum wound bandage associated with a wound of a patient and a control module to provide a negative pressure through the vacuum wound bandage to treat the wound, the canister comprising
 a housing having an interior region to collect waste material from the vacuum wound bandage,
 a latch to couple the housing to the control module, the latch extending through the interior region, and
 a sleeve carried by the housing and positioned within the interior region, wherein a portion of the latch is positioned within the sleeve, and
 wherein the housing has a first vertical wall and a second vertical wall, the sleeve extends from the first vertical wall to the second vertical wall, the first vertical wall has an inlet port to introduce waste material from the vacuum wound bandage into the interior region, the second vertical wall has an outlet port to communicate with a vacuum source of the control module, and the sleeve is lower than the inlet port and the outlet port.

5. A canister adapted for use with a vacuum wound bandage associated with a wound of a patient and a control module to provide a negative pressure through the vacuum wound bandage to treat the wound, the canister comprising
 a housing having an interior region to collect waste material from the vacuum wound bandage, and
 a latch to couple the housing to the control module, the latch extending through the interior region,
 wherein the latch has an actuator and a fastener to couple the housing to the control module in response to rotation of the actuator, and
 wherein the fastener has a pair of canted lugs to cam against the control module in response to rotation of the actuator.

6. A canister adapted for use with a vacuum wound bandage associated with a wound of a patient and a control module to provide a negative pressure through the vacuum wound bandage to treat the wound, the canister comprising
 a housing having an interior region to collect waste material from the vacuum wound bandage, and
 a latch to couple the housing to the control module, the latch extending through the interior region,
 wherein the latch has an actuator and a fastener to couple the housing to the control module in response to rotation of the actuator,
 wherein the actuator has a shaft coupled to the fastener and positioned within the interior region,
 wherein the latch has a retainer coupled to the shaft to maintain the shaft within the interior region, and
 wherein the retainer has a clip and a disk having a groove, and the clip is positioned within the groove to engage the housing.

* * * * *